(12) United States Patent
Tung et al.

(10) Patent No.: US 7,053,220 B2
(45) Date of Patent: May 30, 2006

(54) HYDROXYALKANOYL AMINOPYRAZOLES AND RELATED COMPOUNDS

(75) Inventors: Jay S. Tung, Belmont, CA (US); Ashley C. Guinn, Pacifica, CA (US); Eugene D. Thorsett, Half Moon Bay, CA (US); Michael A. Pleiss, Sunnyvale, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 199 days.

(21) Appl. No.: 10/355,700

(22) Filed: Jan. 31, 2003

(65) Prior Publication Data

US 2004/0006085 A1    Jan. 8, 2004

Related U.S. Application Data

(60) Provisional application No. 60/353,214, filed on Feb. 1, 2002.

(51) Int. Cl.
*C07D 285/135* (2006.01)
(52) U.S. Cl. .................................................. 548/139
(58) Field of Classification Search ................. 548/139
See application file for complete search history.

(56) References Cited

OTHER PUBLICATIONS

Database Cas Online on STN, Chem. Abstr., Accession No. 1972:140733, Khimiya Geterotsiklicheskikh Soedinenii (Luknitskii et al.) (1972), abstract.*
International Search Report dated Jun. 19, 2003.
Guameri, et al., Database CAS Online on STN, Chem. Abstr., Accessinon No. 1974:536478, Gazzetta Chimica Italiana, abstract.

* cited by examiner

*Primary Examiner*—Joseph K. McKane
*Assistant Examiner*—Rebecca Anderson
(74) *Attorney, Agent, or Firm*—Howrey LLP; Viola T. Kung

(57) ABSTRACT

This invention is directed to a class of compounds (Formula I) including hydroxyalkanoyl amino pyrazoles, hydroxyalkanoyl amino thiadiazoles, hydroxyalkanoyl amino acid esters, hydroxyalkanoyl amino acid amides, hydroxyalkanoyl amino alcohols, hydroxyalkanoyl amino ketoes, hydroxyalkanoyl amino hydantoins, hydroxyalkanoyl anilines, and hydroxyalkanoyl derivatives of privileged structures. The invention is also directed to a pharmaceutical formation comprising such compound in a pharmaceutically acceptable salt form or prodrug thereof. The invention is further directed to a method for inhibiting β-amyloid peptide release and/or synthesis, a method for inhibiting γ-secretase activity and a method for treating neurological disorders associated with β-amyloid peptide production. The method comprises administering to a host a pharmaceutical formulation comprising an effective amount of a compound of Formula I. The compounds of Formula I are useful in the prevention and treatment of Alzheimer's disease.

7 Claims, No Drawings

HYDROXYALKANOYL AMINOPYRAZOLES AND RELATED COMPOUNDS

This application claims the benefit of U.S. Provisional Application No. 60/353,214, filed Feb. 1, 2002.

FIELD OF THE INVENTION

This invention relates to compounds hydroxyalkanoyl aminopyrazoles and related compounds that inhibit β-amyloid peptide release and/or its synthesis, and, accordingly, have utility in treating Alzheimer's disease.

BACKGROUND OF THE INVENTION

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (βAP) or sometimes Aβ, AβP or β/A4. β-Amyloid peptide was first purified and a partial amino acid sequence was provided by Glenner, et al. (Biochem. Biophys. Res. Commun., 120: 885–890)1984)). The isolation procedure and the sequence data for the first 28 amino acids are described in U.S. Pat. No. 4,666,829.

Several lines of evidence indicate that progressive cerebral deposition of Aβ plays a seminal role in the pathogenesis of AD and can precede cognitive symptoms by years or decades (*Neuron*, 6: 487–498 (1991)). The most important line of evidence is the discovery that missense DNA mutations at amino acid 717 of the 770-amino acid isoform of APP can be found in affected members but not unaffected members of several families with a genetically determined (familial) form of AD (Goate, *Nature*, 349: 704–706 (1990); Chartier Harlan, *Nature*, 353: 844–846 (1989); and Murrell, *Science*, 254: 97099 (1991)) and is referred to as the Swedish variant. A double mutation changing lysine$^{595}$-methionine$^{596}$ to asparagine$^{595}$-leucine$^{596}$ (with reference to the 695 isoform) found in a Swedish family was reported in 1992 (Mullan, *Nature Genet.*, 1:345–347 (1992)). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP and subsequent deposition of its Aβ fragment can cause AD.

Aβ is derived from cleavage of APP by protease systems, collectively termed secretases. APP is first cleaved by β secretase to yield a β stub, which is then cleaved by γ secretase to yield a β-amyloid fragment that is secreted. β secretase generates the N-terminus of Aβ. γ secretase generates C-terminal fragments ending at position 38, 39, 40, 42, and 43 or generating C-terminal extended precursors that are subsequently truncated to the above polypeptides.

U.S. Pat. No. 6,153,652 discloses N-(aryl/heteroaryl/alkyacetyl)amino acid amides, which inhibit β amyloid peptide release and/or its synthesis, and methods for treating Alzheimer's disease with such compounds. U.S. Pat. Nos. 6,191,166 and 6,211,235 each discloses a class of compounds, which inhibit β amyloid peptide release and/or its synthesis, and methods for treating Alzheimer's disease with such compounds. WO 01/19797 discloses hydroxyalkanoyl aminolactams and related structures and method s for inhibiting γ-secretase activity. WO 00/77030 discloses statine-derived tetrapeptide inhibitors of beta-secretase. WO 99/66934 discloses certain cyclic amino acid compounds that inhibit β-amyloid peptide release and/or its synthesis and methods for treating Alzheimer's disease with such compounds.

Despite the progress which has been made in understanding the underlying mechanisms of AD and other β-amyloid peptide related diseases, there remains a need to develop methods and compositions for treatment of the disease. The treatment methods could be based on drugs that are capable of inhibiting β-amyloid peptide release and/or its synthesis in vivo. Methods of treatment could target the formation of Aβ through the enzymes involved in the proteolytic processing of β-amyloid precursor protein. Compounds that inhibit γ-secretase activity, either directly or indirectly, control the production of AP. Such inhibition of γ secretase could thereby reduce production of Aβ, which, thereby, reduces or prevents the neurological disorders associated with β-amyloid peptide.

SUMMARY OF THE INVENTION

This invention is directed to the discovery of a class of compounds which inhibit β-amyloid peptide release and/or its synthesis. The class of compounds having the described properties are defined by formula I below:

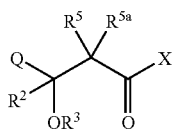

Formula I

The class of compounds includes hydroxyalkanoyl amino pyrazoles, hydroxyalkanoyl amino thiadiazoles, hydroxyalkanoyl amino acid esters, hydroxyalkanoyl amino acid amides, hydroxyalkanoyl amino alcohols, hydroxyalkanoyl amino ketoes, hydroxyalkanoyl amino hydantoins, hydroxyalkanoyl anilines, and hydroxyalkanoyl derivatives of privileged structures. The present invention is also directed to a pharmaceutical formation comprising such compound in a pharmaceutically acceptable salt form or prodrug thereof.

The present invention is directed to a method for inhibiting β-amyloid peptide release and/or synthesis and a method for inhibiting γ-secretase activity. The present invention is also directed to a method for treating neurological disorders associated with β-amyloid peptide production. The method comprises the steps of administering to a host a pharmaceutical formulation comprising an effective amount of a compound of Formula I. The compounds of Formula I are useful in the prevention of AD in patients susceptible to AD and/or in the treatment of patients with AD.

DETAILED DESCRIPTION OF THE INVENTION

This invention is directed to compounds that inhibit β-amyloid peptide release and/or its synthesis. The class of compounds includes hydroxyalkanoyl amino pyrazoles, hydroxyalkanoyl amino thiadiazoles, hydroxyalkanoyl amino acid esters, hydroxyalkanoyl amino acid amides, hydroxyalkanoyl amino alcohols, hydroxyalkanoyl amino ketones, hydroxyalkanoyl amino hydantoins, hydroxyalkanoyl anilines, and hydroxyalkanoyl derivatives of privileged structures (*J. Med. Chem.*, 41:3103 (1998), *J. Comb. Chem.*, 1:388 (1999)). The present invention is also directed to a pharmaceutical formulation comprising such compound.

The class of compounds having the described properties are defined by Formula I below:

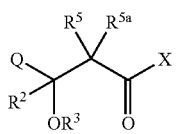

Formula I wherein X is selected from the group consisting of:

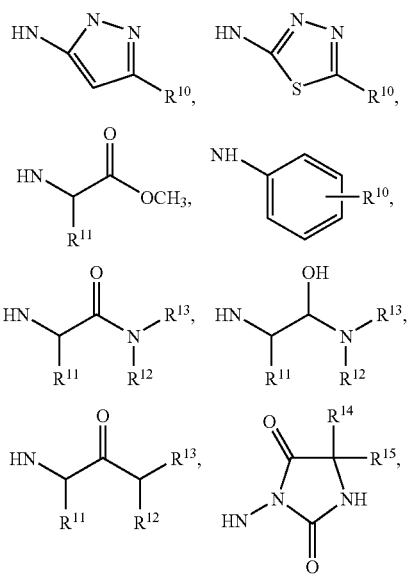

and the following privileged structures:

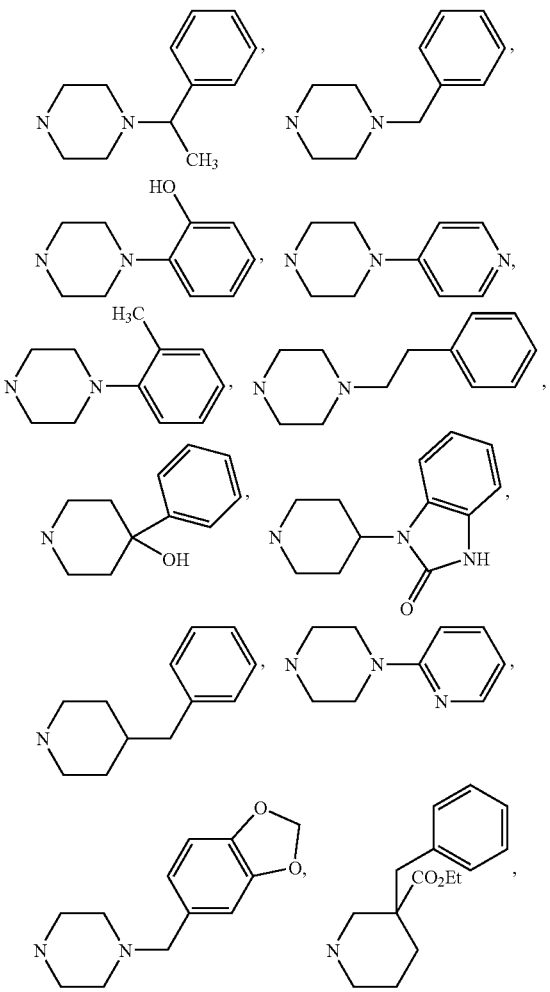

-continued
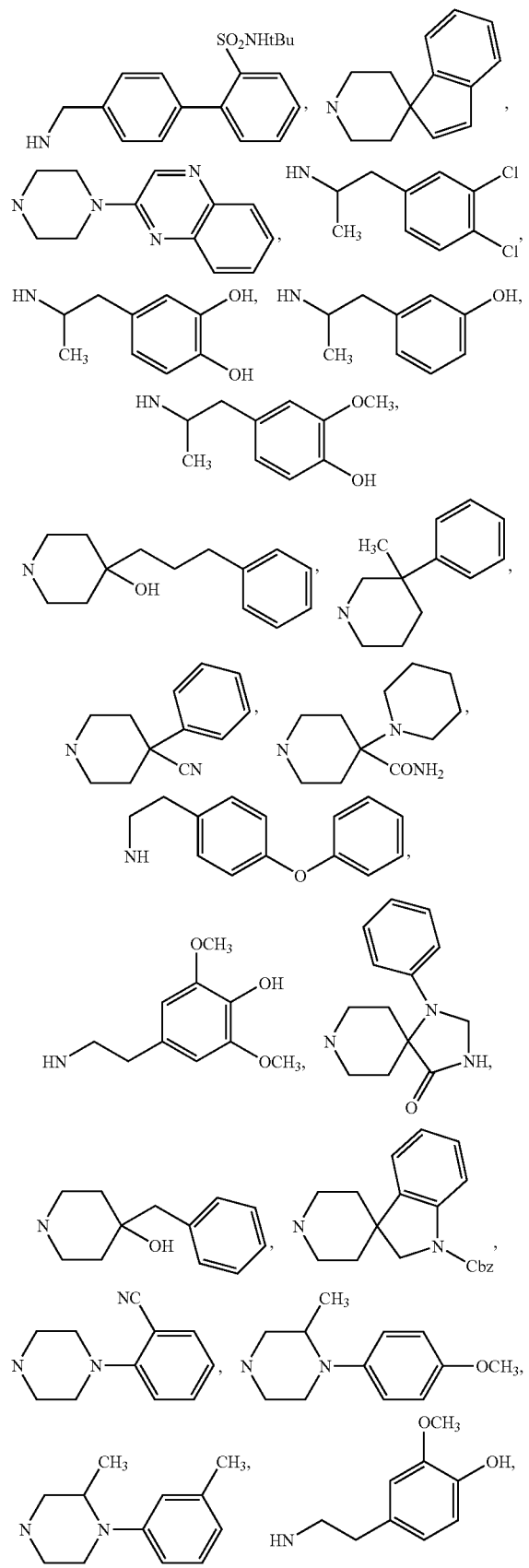
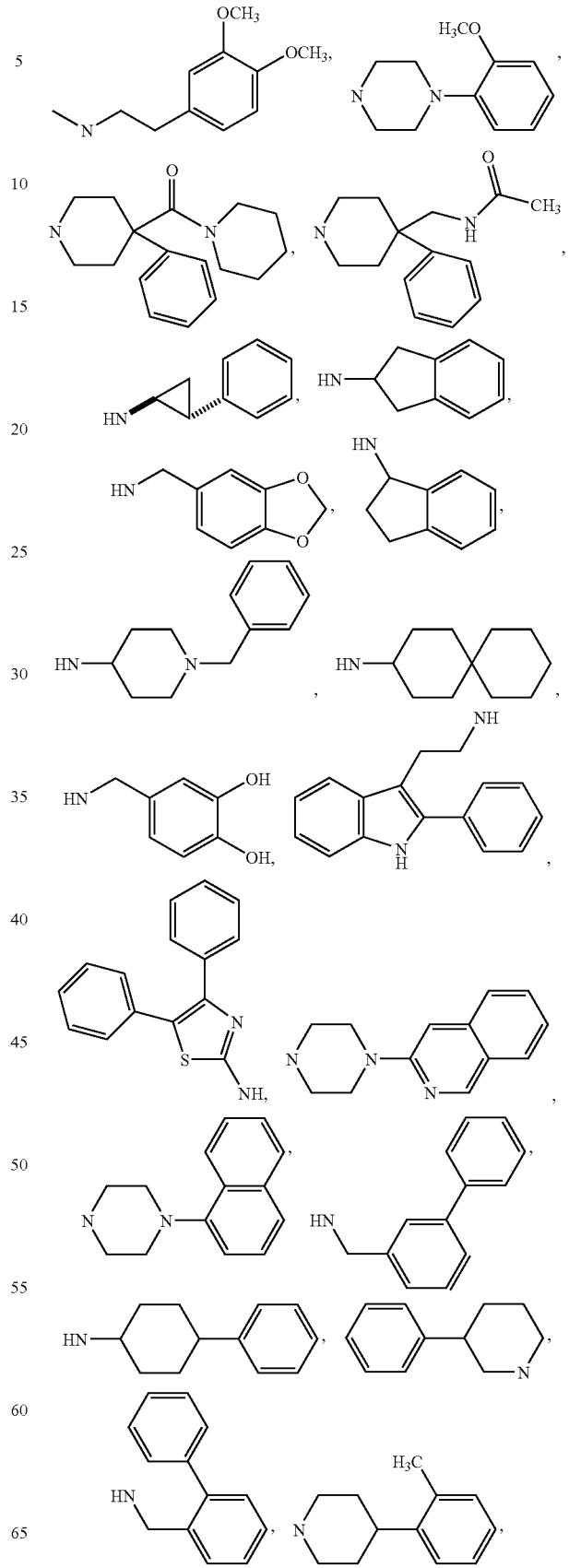

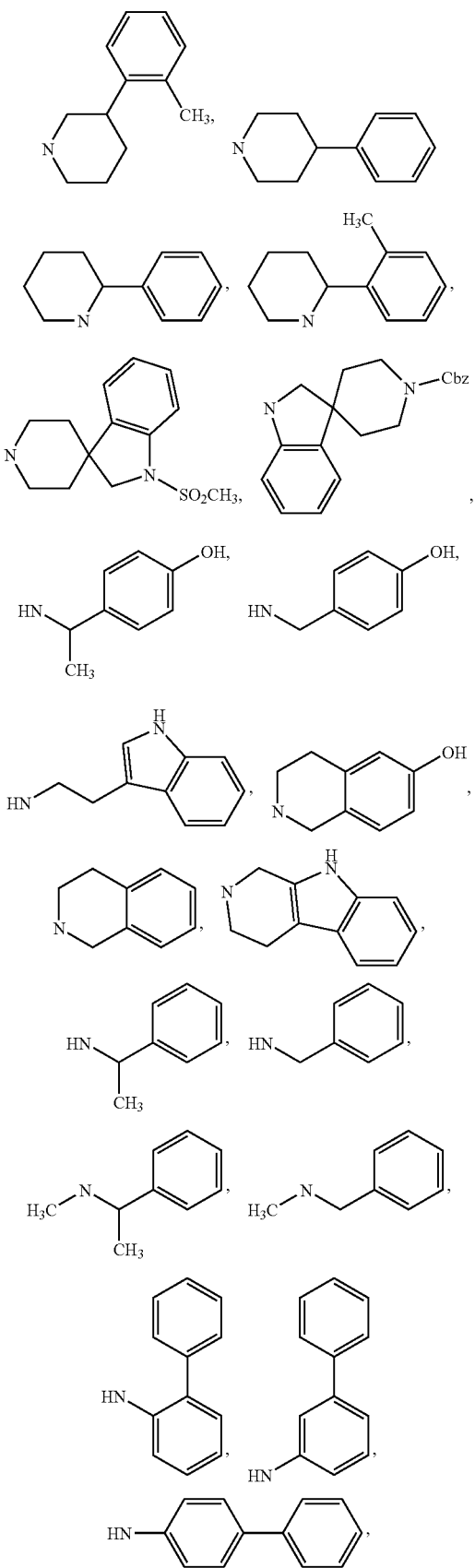
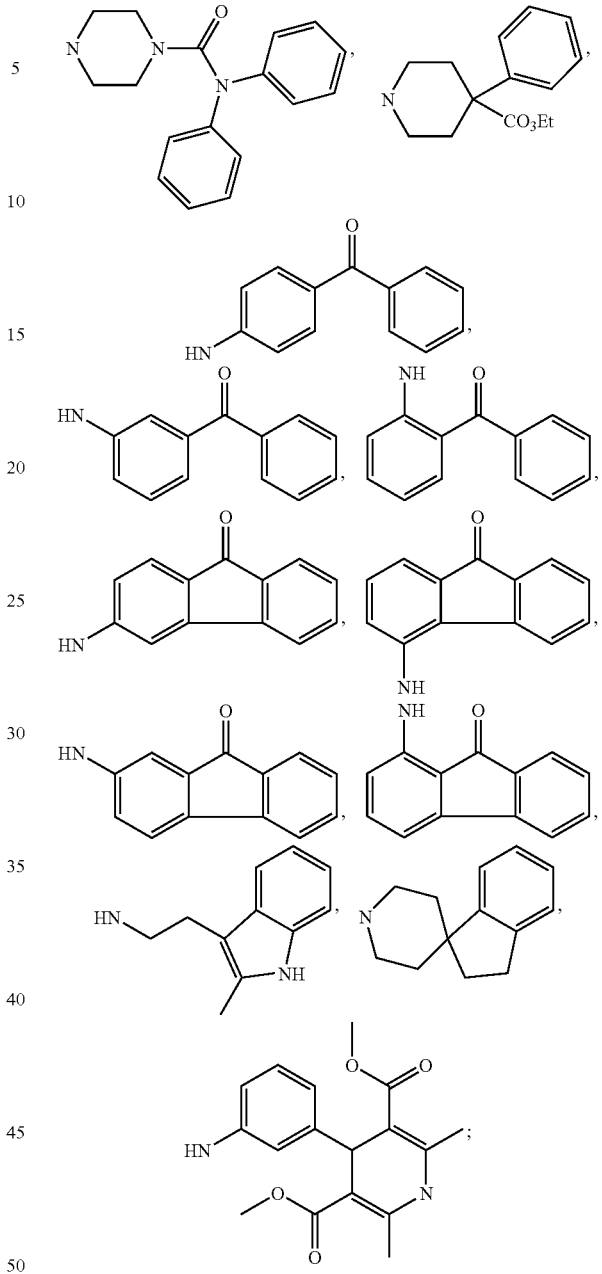

Q is $Q^1$,
 $(C_1–C_3$ alkyl$)$-O-$Q^1$,
 $(C_1–C_3$ alkyl$)$-S-$Q^1$,
 $(C_1–C_3$ alkyl$)$-S(=O)-$Q^1$,
 $(C_1–C_3$ alkyl$)$-S(=O)$_2$-$Q^1$, or
 $(C_1–C_3$ alkyd$)$-N($R^{20}$)-$Q^1$;

$Q^1$, $R^{10}$, and $R^{11}$ are independently $C_1–C_6$ alkyl substituted with 0–3 $R^{1a}$;
 $C_2–C_6$ alkenyl substituted with 0–3 $R^{1a}$;
 $C_2–C_6$ alkynyl substituted with 0–3 $R^{1a}$;
 $C_3–C_{10}$ cycloalkyl substituted with 0–3 $R^{1b}$;
 $C_3–C_{10}$ carbocycle substituted with 0–3 $R^{1b}$;
 $C_6–C_{10}$ aryl substituted with 0–3 $R^{1b}$; or 5 to 10 membered heterocycle containing 1 to 4 heteroatoms selected from nitrogen, oxygen, alnd sulphur, wherein said 5 to 10 membered heterocycle is substituted with 0–3 $R^{1b}$;

$R^{1a}$, at each occurrence, is independently selected from H, $C_1$–$C_6$ alkyl, $OR^{14}$, Cl, F, Br, I, $NR^{15}R^{16}$, $CF_3$;
$C_3$–$C_{10}$ carbocycle substituted with 0–3 $R^{1b}$;
$C_6$–$C_{10}$ aryl substituted with 0–3 $R^{1b}$; and
5 to 10 membered heterocycle containing 1 to 4 heteroatoms selected from nitrogen, oxygen, and sulphur, wherein said 5 to 10 membered heterocycle is substituted with 0–3 $R^{1b}$;

$R^2$ and $R^{12}$ are independently H, methyl, ethyl, propyl, or butyl;
$R^3$ is H, $C_1$–$C_4$ alkyl, —C(=O)($C_1$–$C_4$ alkyl), —C(=S)($C_1$–$C_4$ alkyl), or —C(=O)$NR^{21}R^{22}$;
$R^5$ is H, $OR^{14}$;
$C_1$–$C_6$ alkyl substituted with 0–3 $R^{5b}$;
$C_1$–$C_6$ alkoxy substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ cycloalkyl substituted with 0–3 $R^{5c}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3$R^{5c}$;

$R^{5a}$ is H, $C_1$–$C_4$ alkyl, or $C_2$–$C_4$ alkenyl;
alternatively, $R^5$ and $R^{5a}$ may be combined to form a 3–7 membered cycloalkyl ring substituted with 0–3 $R^{5c}$;

$R^{5b}$, at each occurrence, is independently selected from:
H, $C_1$–$C_6$ alkyl, $CF_3$, $OR^{14}$, Cl, F, Br, I, =O, CN, $NO_2$, $NR^{15}R^{16}$, acetyl, $SCH_3$, S(=O)$CH_3$, S(=O)$_2CH_3$, $C_2$–$C_6$ alkenyl, $C_2$–$C_6$ alkynyl, $C_1$–$C_4$ alkoxy, $C_1$–$C_4$ haloalkyl, $C_1$–$C_4$ haloalkoxy, and $C_1$–$C_4$ haloalkyl-S—,
$C_3$–$C_{10}$ cycloalkyl substituted with 0–3 $R^{5c}$;
$C_3$–$C_{10}$ carbocycle substituted with 0–3 $R^{5c}$;
$C_6$–$C_{10}$ aryl substituted with 0–3 $R^{5c}$; and
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$CH_3$, $C_1$–$C_6$ alkyl, $C_1$–$C_4$ alkoxy, Cl—$C_4$ haloalkyl, $C_1$–$C_4$ haloalkoxy, and $C_1$–$C_4$ haloalkyl-S—;

$R^{13}$, at each occurrence, is independently $C_1$–$C_6$ alkyl, alkeny, or alkynyl optionally substituted with $C_6$–$C_{10}$ aryl substituted with 0–3 $R^{5c}$;

$R^{14}$, at each occurrence, is independently selected from H, phenyl, benzyl, $C_1$–$C_6$ alkyl, and $C_2$–$C_6$ alkoxyalkyl;

$R^{15}$, at each occurrence, is independently selected from H, $C_1$–$C_6$ alkyl, phenyl, benzyl, phenethyl, ($C_1$–$C_6$ alkyl)-C(=O)—, ($C_1$–$C_6$ alkyl)-O—C(=O)— and ($C_1$–$C_6$ alkyl)-S(=O)$_2$—; and, $R^{16}$, at each occurrence, is independently selected from H, $C_1$–$C_6$ alkyl, phenyl, benzyl, phenethyl, ($C_1$–$C_6$ alkyl)-C(=O)—, ($C_1$–$C_6$ alkyl)-O—C(=O)— and ($C_1$–$C_6$ alkyl)-S(=O)$_2$—.

In a preferred embodiment:
$R^{10}$ is —C(CH$_3$)$_2$ phenyl;
$R^{11}$ is —CH$_2$CH$_2$CH$_2$CH$_3$;
$R^{12}$ is H or methyl; and
$R^{13}$ is —(CH$_2$)$_5$ phenyl.

In another preferred embodiment:
Q is $Q^1$;
$R^{1b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, and ($C_1$–$C_6$ alkyl)-O—C(=O)—;
$R^2$ is H, methyl, or ethyl;
$R^5$ is H, $OR^{14}$;
$C_1$–$C_6$ alkyl substituted with 0–3 $R^{5b}$;
$C_2$–$C_6$ alkenyl substituted with 0–3 $R^{5b}$; or
$C_2$–$C_6$ alkynyl substituted with 0–3 $R^{5b}$;
$R^{5a}$ is H, methyl, ethyl, propyl, butyl, or $C_2$–$C_4$ alkenyl;
alternatively, $R^5$ and $R^{5a}$ may be combined to form a $C_4$–$C_7$ cycloalkyl ring;
$R^{5b}$, at each occurrence, is independently selected from:
H, methyl, ethyl, propyl, butyl, $CF_3$, $OR^{14}$, Cl, F, Br, I, =O, $NR^{15}R^{16}$,
$C_3$–$C_7$ cycloalkyl substituted with 0–3 $R^{5c}$;
$C_3$–$C_7$ carbocycle substituted with 0–3 $R^{5c}$;
phenyl substituted with 0–3 $R^{5c}$; and
5 to 7 membered heterocycle containing 1 to 4 heteroatoms selected from nitrogen, oxygen, and sulphur, wherein said 5 to 7 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O) $CH_3$, S(=O)$_2CH_3$, $C_1$–$C_4$ alkyl, $C_1$–$C_3$ alkoxy, $C_1$–$C_2$ haloalkyl, and $C_1$–$C_2$ haloalkoxy;

$R^{12}$, at each occurrence, is independently H, or methyl;

$R^{14}$, at each occurrence, is independently selected from H, phenyl, benzyl, $C_1$–$C_4$ alkyl, and $C_2$–$C_4$ alkoxyalkyl;

$R^{15}$, at each occurrence, is independently selected from H, methyl, ethyl, propyl, butyl, phenyl, benzyl, and phenethyl; and, $R^{16}$, at each occurrence, is independently selected from H, OH, methyl, ethyl, propyl, butyl, phenyl, benzyl, phenethyl, CH$_3$CH$_2$C(=O)—, CH$_3$C(=O)—, CH$_3$CH$_2$OC(=O)—, CH$_3$OC(=O)—, CH$_3$CH$_2$S(=O)$_2$— and CH$_3$S(=O)$_2$—.

In another preferred embodiment:
Q is $Q^1$;
$Q^1$, $R^{10}$ and $R^{11}$ are independently $C_1$–$C_6$ alkyl substituted with 0–3 $R^{1a}$;
$C_2$–$C_6$ alkenyl substituted with 0–3 $R^{1a}$;
$C_2$–$C_6$ alkynyl substituted with 0–3 $R^{1a}$;
$C_3$–$C_6$ cycloalkyl substituted with 0–3 $R^{1b}$;
Phenyl substituted with 0–3 $R^{1b}$; or
5 to 6 membered heterocycle containing 1 to 4 heteroatoms selected from nitrogen, oxygen, and sulphur, wherein said 5 to 6 membered heterocycle is substituted with 0–3 $R^{1b}$;
$R^{1a}$, at each occurrence, is independently selected from
H, methyl, ethyl, propyl, butyl, $OR^{14}$, Cl, F, Br, I, $NR^{15}R^{16}$, $CF_3$;
$C_3$–$C_6$ carbocycle substituted with 0–3 $R^{1b}$;
phenyl substituted with 0–3 $R^{1b}$; and
5 to 6 membered heterocycle containing 1 to 4 heteroatoms selected from nitrogen, oxygen, and sulphur, wherein said 5 to 6 membered heterocycle is substituted with 0–3 $R^{1b}$;
$R^2$ is H or methyl;

R⁵ is H, OR¹⁴;
  $C_1$–$C_4$ alkyl substituted with 0–1 $R^{5b}$;
  $C_2$–$C_4$ alkenyl substituted with 0–1 $R^{5b}$; or
  $C_2$–$C_4$ alkynyl substituted with 0–1 $R^{5b}$;
$R^{5a}$ is H, methyl, ethyl, propyl, or butyl;
alternatively, $R^5$ and $R^{5a}$ may be combined to form a cyclobutyl, cyclopentyl, cyclohexyl, or cycloheptyl ring;
$R^{5b}$, at each occurrence, is independently selected from:
  H, methyl, ethyl, propyl, butyl, $CF_3$, $OR^{14}$, Cl, F, =O, $NR^{15}R^{16}$,
  $C_3$–$C_7$ cycloalkyl substituted with 0–3 $R^{5c}$;
  $C_3$–$C_7$ carbocycle substituted with 0–3 $R^{5c}$;
  phenyl substituted with 0–3 $R^{5c}$; and
  5 to 7 membered heterocycle containing 1 to 4 heteroatoms selected from nitrogen, oxygen, and sulphur, wherein said 5 to 7 membered heterocycle is substituted with 0–3 $R^{5c}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;
$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;
$R^{12}$, at each occurrence, is independently H, or methyl;
$R^{14}$, at each occurrence, is independently selected from H, phenyl, benzyl, methyl, ethyl, propyl, and butyl;
$R^{15}$, at each occurrence, is independently selected from H, methyl, ethyl, propyl, or butyl; and,
$R^{16}$, at each occurrence, is independently selected from H, OH, methyl, ethyl, propyl, butyl, phenyl, benzyl, and phenethyl.

In a further preferred embodiment:
Q is —$CH_3$, —$CH_2CH_3$, —$CH_2CH_2CH_3$, —$CH_2CH_2CH_2CH_3$, —$CH_2CH_2CH_2CH_3$, —$CH_2CH_2CH_2CH_2CH_3$, —$CH_2CH_2CH_2CH_2CH_2CH_3$, —$CH(CH_3)_2$, —$CH(CH_3)CH_2CH_3$, —$CH_2CH(CH_3)_2$, —$CH_2C(CH_3)_3$, $CF_3$, —$CH_2F_3$, —$CH_2CH_2CF_3$,
  —$CH=CH_2$, —$CH_2CH=CH_2$, —$CH_2C(CH_3)=CH_2$, —$CH_2CH=C(CH_3)_2$, —$CH_2CH_2CH=CH_2$, —$CH_2CH_2C(CH_3)=CH_2$, cis-$CH_2CH=CH(CH_3)$, cis-$CH_2CH_2CH=CH$ ($CH_3$); trans-$CH_2CH=CH$ ($CH_3$), trans $CH_2CH_2CH=CH(CH_3)$, —C≡CH, —$CH_2C≡CH$, —$CH_2C≡C(CH_3)$,
  cyclopropyl-, cyclobutyl-, cyclopentyl-, cyclohexyl-, cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$—, cyclohexyl-$CH_2CH_2$—,
  phenyl-, 2-F-phenyl-, 3-F-phenyl-, 4-F-phenyl-, 4-methoxyphenyl-, 4-ethoxyphenyl-, 4 propoxyphenyl-, phenyl-$CH_2$—, (2-F-phenyl)$CH_2$—, (3-F-phenyl)$CH_2$—, (4-F-phenyl)$CH_2$—, (2-Cl-phenyl) $CH_2$—, (3-Cl-phenyl)$CH_2$—, (4-Cl-phenyl)$CH_2$—,
  (2,3-diF-phenyl)$CH2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)(2,4-$CH_2$—,diCl-phenyl)$CH_2$—, (2,5-diCl-phenyl)$C_2$—, (2,6-diCl-phenyl)$CH_2$—, (3,4-diCl-phenyl)(3,5-$CH_2$—,diCl-phenyl)$CH_2$—, (3-F-4-Cl-phenyl)$CH_2$—, (3-F-5-Cl-phenyl)$CH_2$—, (3-Cl-4-F-phenyl)$CH_2$—,
  2-furanyl-$CH_2$—, 3-furanyl-$CH_2$—, 2-thienyl-$CH_2$—, 3-thienyl-$CH_2$—, 2-pyridyl-$CH_2$—, 3-pyridyl-$CH_2$—, 4-pyridyl-$CH_2$—, 1-imidazolyl-$CH_2$—, 2-oxazolyl-$CH_2$—, 4-oxazolyl-$CH_2$—, 5-oxazolyl-$CH_2$—, 3-isoxazolyl-$CH_2$—, 4-isoxazolyl-$CH_2$—, 5-isoxazolyl-$CH_2$—,
  phenyl-$CH_2CH_2$—, (2-F-phenyl)$CH_2H_2$—, (3-F-phenyl)$CH_2H_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2H_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-phenyl)$CH_2CH_2$—, (3-F-5-Cl-phenyl)$CH_2CH_2$—;
  furanyl-$CH_2CH_2$—, thienyl-$CH_2CH_2$—, pyridyl-$CH_2CH_2$—, 1-imidazolyl-$CH_2CH_2$—, oxazolyl-$CH_2CH_2$—, isoxazolyl-$CH_2CH_2$—, 3,5-dimethylisoxazol-4-yl-$CH_2CH_2$—, phenyl-propyl-;
  benzyl-$CH(NH_2)$—, benzyl-$CH(NHC(=O)$—O-tBu)-, benzyloxy-$CH_2$—, pyrrolidin-2-yl-, or 3-t-butoxycarbonylpyrrolidin-2-yl-;
$R^2$ is H or methyl;
$R^5$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2H_2CH_3$, —$CH_2CH(CH_3)CH_2CH_3$, —$CH_2CH_2CH(CH_3)_2$, —$CH(CH_2CH_3)_2$,
  —$CF_3$, —$CH_2CF_3$, —$CH_2CH_2CF_3$, —$CH_2CH_2CH_2CH_3$, —$CH_2CH_2CH_2CH_2CF_3$,
  —$CH=CH_2$, —$CH_2CH=CH_2$, —$CH_2CH_2CH=CH_2$, —$CH=CHCH_3$, cis-$CH_2CH=CH(CH_3)$, trans-$CH_2CH=CH(CH_3)$, trans-$CH_2CH=CH(C_6H_5)$, —$CH_2CH=C(CH_3)_2$, cis-$CH_2CH=CHCH_2CH_3$, trans-$CH_2CH=CHCH_2CH_3$, cis-$CH_2CH_2CH=CH(CH_3)$, trans-$CH_2CH_2CH=CH$ ($CH_3$), trans-$CH_2CH=CHCH_2(C_6H_5)$,
  —C≡CH, —$CH_2C≡CH$, —$CH_2C≡C(CH_3)$, —$CH_2C≡C(C_6H_5)$, —$CH_2CH_2C≡CH$, —$CH_2CH_2C≡C(CH_3)$, —$CH_2CH_2C≡C(C_6H_5)$, —$CH_2CH_2CH_2C≡CH$, —$CH_2CH_2CH_2C≡C(CH_3)$, —$CH_2CH_2CH_2C≡C(C_6H_5)$,
  cyclopropyl-$CH_2$—, cyclobutyl-$CH_2$—, cyclopentyl-$CH_2$—, cyclohexyl-$CH_2$—, (2-$CH_3$-cyclopropyl)$CH_2$—, (3-$CH_3$-cyclobutyl)$CH_2$—, cyclopropyl-$CH_2CH_2$—, cyclobutyl-$CH_2CH_2$—, cyclopentyl-$CH_2CH_2$—, cyclohexyl-$CH_2CH_2$—, (2-$CH_3$-cyclopropyl)$CH_2CH_2$—, (3-$CH_3$-cyclobutyl)$CH_2CH_2$—,
  phenyl-$CH_2$—, (2-F-phenyl)$CH_2$—, (3-F-phenyl)$CH_2$—, (4-F-phenyl)$CH_2$—, (3,5-diF-phenyl)$CH_2$—, 2-furanyl-$CH_2$—, 3-furanyl-$CH_2$—, 2-thienyl-$CH_2$—, 3-thienyl-$CH_2$—, 2-pyridyl-$CH_2$—, 3-pyridyl-$CH_2$—, 4-pyridyl-$CH_2$—, 1-imidazolyl-$CH_2$—, 2-oxazolyl-$CH_2$—, 4-oxazolyl-$CH_2$—, 5-oxazolyl-$CH_2$—, 3-isoxazolyl-$CH_2$—, 4-isoxazolyl-$CH_2$—, 5-isoxazolyl-$CH_2$—,
  phenyl-$CH_2CH_2$—, (2-F-Phenyl)$CH_2CH_2$—, (3-F-phenyl)$CH_2CH_2$—, (4-F-phenyl)$CH_2CH_2$—, furanyl-$CH_2CH_2$—, thienyl-$CH_2CH_2$—, pyridyl-$CH_2CH_2$—, 1-imidazolyl-$CH_2CH_2$—, oxazolyl-$CH_2CH_2$—, isoxazolyl-$CH_2CH_2$—;
methoxy, ethoxy, propoxy, or butoxy;
$R^{5a}$ is H;
alternatively, $R^5$ and $R^{5a}$ may be combined to form cyclopentyl, cyclohexyl, or cycloheptyl.

Definition

The term "β-amyloid peptide" refers to a 39–43 amino acid peptide having a molecular weight of about 4.2 kD, which peptide is substantially homologous to the form of the protein described by Glenner, et al. (*Biochem. Biophys. Res. Commun.,* 120:885–890 (1984)) including mutations and post-translational modifications of the normal β-amyloid peptide. In whatever form, the β-amyloid peptide is approximately a 39–43 amino acid fragment of a large membrane-spanning glycoprotein, referred to as the β-amyloid precursor protein (APP). Its 43-amino acid sequence is:

1
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr (SEQ ID NO: 1)

or a sequence which is substantially homologous thereto.

"Alkyl" refers to monovalent alkyl groups preferably having from 1 to 10 carbon atoms and more preferably 1 to 6 carbon atoms. This term is exemplified by groups such as methyl, ethyl, n-propyl, iso-propyl, n-butyl, iso-butyl, n-hexyl, and the like. The use of the notation "C" followed by a numerical range preceding a defined term, indicates a range of atoms intended to add further to the definition. e.g., $(C_{1-6})$alkyl defines an alkyl group having from 1 to 6 (inclusive) carbon atoms.

Unless otherwise constrained by a limitation of the alkyl group, alkyl can optionally be substituted with from 1 to 3 substituents selected from the group consisting of hydroxy, $(C_{1-3})$ alkoxy, $(C_{1-3})$alkylthioxy, halo, acyl, acyloxy, phenyl optionally substituted with 1 to 2 halo atoms and trifluoromethyl.

"Arylalkyl" refers to aryl -alkylene-groups preferably having from 1 to 6 carbon atoms in the alkylene moiety and from 6 to 10 carbon atoms in the aryl moiety. Such arylalkyl groups are exemplified by benzyl, phenethyl and the like.

"Alkoxy" refers to the group "alkyl-O—" where alkyl is as defined herein. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH$_2$), n-propenyl (—CH$_2$CH=CH$_2$), iso-propenyl (—C(CH$_3$)=CH$_2$), but-2-enyl (—CH$_2$CH=CHCH$_3$) and the like.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—CH$_2$—C≡CH) and the like.

"Acyl" refers to the groups alkyl-C(O)—, aryl-C(O)—, and heteroaryl-C(O)— where alkyl, aryl and heteroaryl are as defined herein.

"Acylamino" refers to the group —C(O)NRR where each R is independently hydrogen or alkyl where alkyl is as defined herein.

"Aminoacyl" refers to the group —NRC(O)R where each R is independently hydrogen or alkyl where alkyl is as defined herein.

"Acyloxy" refers to the groups alkyl-C(O)O—, aryl-C(O)O—, heteroaryl-C(O)O—, and heterocyclic-C(O)O— where alkyl, aryl, heteroaryl and heterocyclic are as defined herein.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

Unless otherwise constrained by the definition for the aryl substituent, such aryl groups can optionally be substituted with from 1 to 3 substituents selected from the group consisting of hydroxy, acyl, acyloxy, alkyl, alkoxy, alkenyl, alkynyl, amino, aminoacyl, aryl, aryloxy, carboxyl, alkoxycarbonyl, acylamino, cyano, halo, nitro, heteroaryl, trihalomethyl and the like. Preferred substituents include alkyl, alkoxy, halo, cyano, nitro, trihalomethyl, and thioalkoxy.

"Aryloxy" refers to the group aryl-O— wherein the aryl group is as defined above including optionally substituted aryl groups as also defined above.

The terms "amide" and "amido" refer to a functional group containing a carbon atom double-bonded to an oxygen atom and additionally singly bonded to a nitrogen atom [—C(O)—N]. "Primary" amide describes an unsubstituted amide group [—C(O)—NH$_2$]. "Secondary" and "tertiary" amides are amides in which nitrogen is substituted with one and two non-hydrogen groups respectively.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkenyl" refers to cyclic alkenyl groups of from 4 to 8 carbon atoms having a single cyclic ring and at least one point of internal unsaturation which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Halo" or "halogen" refers to fluoro, chloro, bromo and iodo and preferably is either chloro or fluoro.

"Heterocycle" or "heterocyclic" refers to a monovalent saturated or unsaturated group having a single ring or multiple condensed rings, from 1 to 8 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 3 substituents selected from the group consisting of alkyl, alkoxy, aryl, aryloxy, halo, nitro, heteroaryl, thioalkoxy, thioaryloxy and the like. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

"Thiol" refers to the group —SH.

"Thioalkoxy" refers to the group —S-alkyl.

"Thioaryloxy" refers to the group aryl-S— wherein the aryl group is as defined above including optionally substituted aryl groups as also defined above.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Privileged structures" are defined in J. Med. Chem. 41: 3103 (1998); they are derivatives of frequently occurring hydrophobic double-ring structure units, including, but not limited to benzodiazepines, spiroindanylpiperidine, etc. It is found that the presence of hydrophobic double-ring systems contributes to the receptor affinity of many biogenic amine antagonists. It is suggested that this motif bind to acccessory binding sites of a predominantly hydrophobic nature located next to the receptor for the corresponding agonist.

Synthesis and Preparation of Compounds Having Formula I

The compounds of the present invention can be prepared in a number of ways known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Hydroxyalkanoic acids can be prepared according to WO 01/19797. An hydroxyalkanoic acid can be coupled to an appropriate amino moiety of an intermediate using methods commonly used in peptide syntheses, such as DCC, EDCI, CDI, BOP, PyBOP, HOAT, HATU, HBTU, POCl$_3$, and phenyl ester mediated coupling, as described in A. R. Chamberlin, Chem. Rev. 97:2243–2266 (1997).

Construction of Hydroxyalkanoyl Amino Pyrazoles.

A variety of 5' hydroxyalkanoyl substituted amino pyrazoles can be prepared using the corresponding carboxylic acids in this fashion.

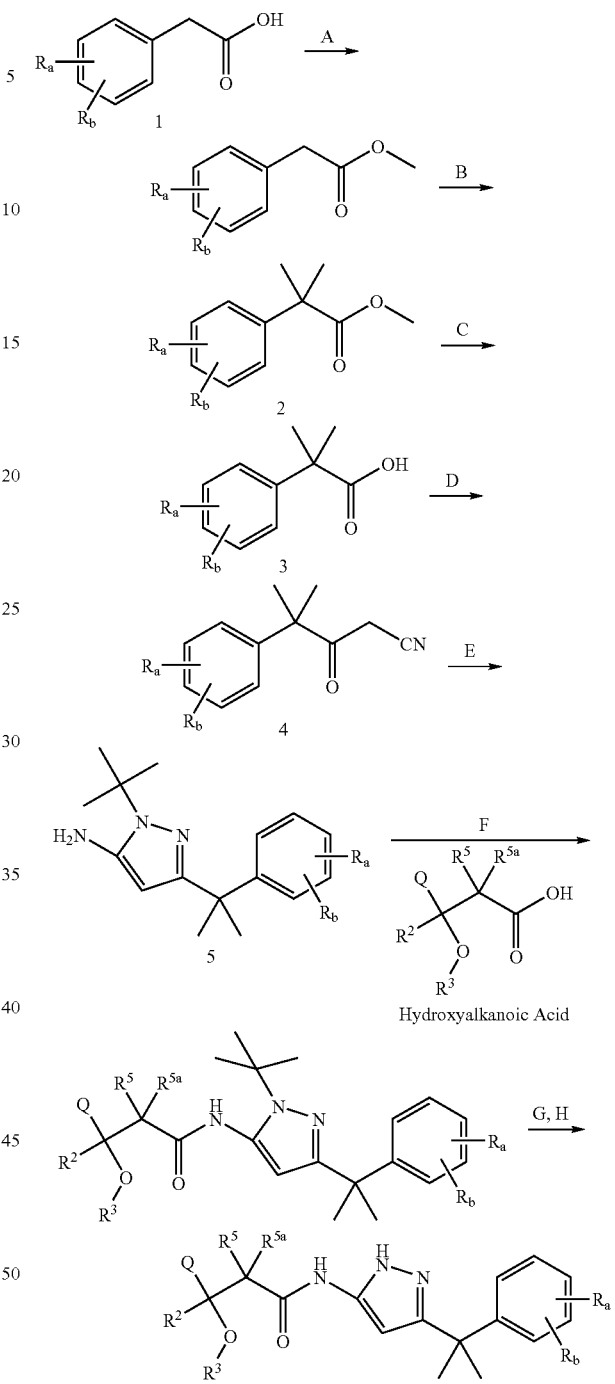

Method A

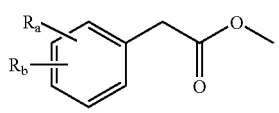

A solution of 0.11 mole of substituted phenylacetic acid in 200 mL of MeOH was prepared. Gaseous HCl was bubbled through the reaction solution for 4 min. After bubbling HCl$_{(gas)}$, the solution was stirred at room temperature for 17 hrs. The solvent was then stripped off by rotary evaporation. The remaining liquid was quenched with saturated NaHCO$_3$ $_{(aq)}$ to ~pH 8 and extracted with EtOAc (3×100 mL). The combined organic extracts were dried over MgSO$_4$ and vacuum filtered. The filtrate was rotary evaporated and dried under vacuum to afford a clear colorless liquid as product 1.

Method B

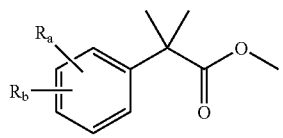

2

A suspension of 0.42 mole (4.0 eq.) of NaH in 500 mL of dry DMF was cooled to −10° C. and 0.11 moles (1.0 eq.) of phenylacetic acid methyl ester 1 was added. The reaction mixture was stirred for 10 min followed by the careful addition of 0.42 moles (4.0 eq.) of methyl iodide. After stirring the reaction mixture, as bath warmed to room temperature, for 16 hrs, 100 mL of water was added followed by 200 mL of 0.1 M HCl. The solution was extracted with EtOAc (3×200 mL). The combined organic extracts were washed with 0.1 M HCl (2×100 mL), followed by drying over MgSO$_4$ and vacuum filtering. The filtrate was rotary evaporated and the crude mixture was flash chromatographed on silica using 5% EtOAc/hexanes as eluent to afford a light yellowish liquid as the α,α-dimethyl-phenylacetic acid methyl ester 2 (69–96% yield after 2 steps).

Method C

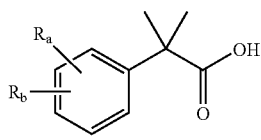

3

A solution of 0.10 mole (1 eq.) of α,α-dimethylphenylacetic acid methyl ester 2 in 150 mL of MeOH and 50 mL of water was added 1.02 mole (10.1 eq.) of KOH pellets. After stirring at room temperature for 3.5 days, the methanol was stripped off by rotary evaporation. To the residual liquid was added 100 mL of water and enough concentrated HCl to bring to ~pH 3. The aqueous solution was extracted with Et$_2$O (3×100 mL). The combined organic layers were dried over MgSO$_4$ and vacuum filtered. The filtrate was rotary evaporated and dried under vacuum to give a white solid as α,α-dimethylphenylacetic acid 3 (87–89%).

Method D

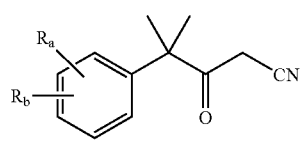

4

In a dried 250 mL round bottom flask, a solution of 0.088 mole (1.0 eq.) of α,α-dimethylphenylacetic acid 3 in 100 mL of dry tetrahydrofuran THF was prepared. To the reaction solution was added 0.114 mole (1.3 eq.) of N,N'-carbonyldiimidazole. The reaction solution was stirred for 1 hr at room temperature.

In a separate 1 L round bottom flask, a solution of 0.264 mole (3.0 eq.) of cyanoacetic acid in 600 mL of dry THF was cooled to −78° C. and 0.526 mole (6.0 eq.) of isopropylmagnesium chloride was added. The reaction mixture was stirred in bath for 25 min and the imidazolide solution prepared via above method was added. After addition, the reaction mixture was stirred, as bath warmed to room temperature, for 17 hrs. At that time, 400 mL of water was added followed by enough concentrated acetic acid to bring to ~pH 5. The acidified solution was extracted with Et$_2$O (3×100 mL). The combined organic extracts were dried over MgSO$_4$ and vacuum filtered. The filtrate was concentrated by rotary evaporation. The crude material was flash chromatographed on silica with 20% EtOAc/hexanes to give a yellowish oil as ketonitrile product 4 (46–67%).

Method E

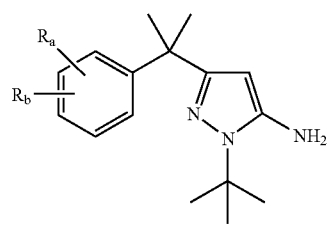

5

A solution of 0.088 (1.0 eq.) mole of ketonitrile 4, 0.353 mole (4.0 eq.) of tert-butylhydrazine, and 0.44 mole (5.0 eq.) of triethylamine in 100 mL of absolute ethanol was refluxed for 4 days. After cooling to room temperature, the reaction solution was rotary evaporated. The residue was taken up in 100 mL of water and was extracted with EtOAc (3×100 mL). The combined organic extracts were dried over MgSO$_4$ and vacuum filtered. The filtrate was rotary evaporated. The residual crude material was flash chromatographed on silica with 10% EtOAc/hexanes to afford amino pyrazole 5 (50–87%).

Method F

General Procedure for POCl$_3$ Coupling.

A solution of 2.3 mmole (1.0 eq) of amine (pyrazoles, thiadiazole, anilines) and 2.3 mmole (1.0 eq) of hydroxyalkanoic acid in 8.0 mL of dry pyridine was stirred at −10° C. as 2.6 mmole (1.1 eq) of POCl$_3$ was added dropwise. After 15 min, the reaction mixture was poured into 125 mL of 1M HCl and extracted with EtOAc. The organic layer was dried over MgSO$_4$, filtered and the solvent removed by rotary evaporation. Purification of the material on silica gel using 3:7 EtOAc-hexanes as eluant afforded 1.4 mmole (59%) of product.

Method G

A solution of 2.0 mmoles (1.0 eq.) of N-tert-butyl protected pyrazole 6 in 10 mL of formic acid is refluxed for 15 min. The reaction solution is cooled to room temperature and is added dropwise to saturated NaHCO$_{3(aq)}$. After ensuring ~pH 8, the quenched solution is extracted with EtOAc (3×100 mL). The combined organic extracts are rotary evaporated. The residue is dissolved in 10 mL of MeOH and 0.80 mmole (0.4 eq.) of LiOH.H$_2$O added. After stirring the mixture at room temperature for 20 min, the solvent is rotary evaporated. The residue is taken up in 40 mL of water and 2 mL of 1 M HCl is added, followed by enough saturated NaHCO$_{3(aq)}$ to raise to ~pH 8. The mixture is extracted with EtOAc (3×70 mL). The combined organic extracts are dried over MgSO$_4$ and vacuum filtered. The filtrate is rotary evaporated and the crude material is flash chromatographed on silica with 3% MeOH/CH$_2$Cl$_2$ to yield the desired product.

Method H

If R$_3$=H in the final compound, removal of the appropriately used protecting group may be necessary. See Protective Groups In Organic Synthesis (Theodora W. Greene and Peter G. M. Wuts, Wiley and Sons)

Construction of Hydroxyalkanoyl Amino Thiadiazoles:

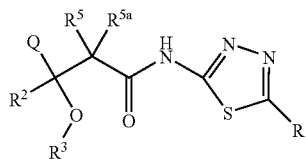

A variety of 5' subtituted thiadiazoles can be prepared via the corresponding substituted carboxylic acids.

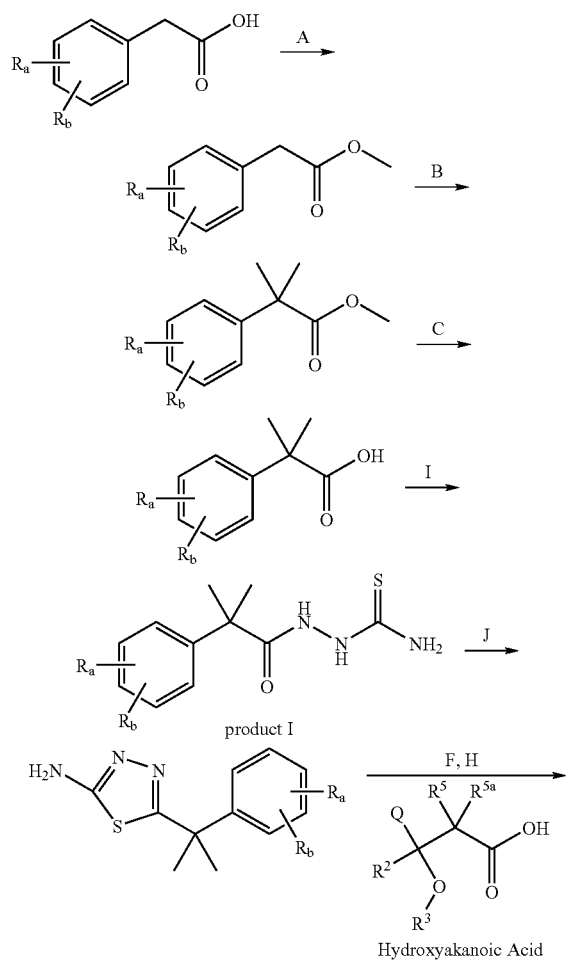

-continued

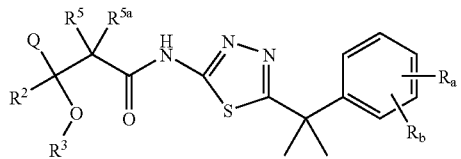

Method I

To a stirred solution of carboxylic acid (42.4 mmol) in anhydrous dichloromethane (40 ml) was added oxalyl chloride (3.70 ml, 42.4 mmol), followed by addition of 0.5 ml of DMF. The reaction mixture was stirred until bubbling ceased.

The reaction mixture was evaporated to dryness, the residue was dissolved in anhydrous THF and was added dropwise to a suspension of thiosemicarbazide (7.73 g, 84.8 mmol) in anhydrous THF cooled in an ice-water bath. The reaction mixture was allowed to warm to room temperature and stirred for 18 h. The reaction mixture was filtered and concentrated to yield the desired product.

Method J

The product from Method I (4.7466 g, 20 mmol), methanesulfonic acid (2 ml, 30 mmol) and toluene (60 ml) were refluxed for 5 h, and allowed to cool down. The crystals were filtered off, and washed with toluene followed by diethyl ether. The resulting solid was placed in a beaker, and treated with concentrated ammonium hydroxide. The precipitate was filtered off, washed with water, and air-dried to yield the desired product.

Construction of Hydroxyalkanoyl Derivatives of Privileged Structures:

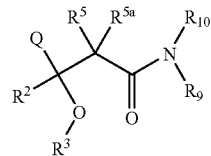

The definition of Privileged structures can be found in *J. Med. Chem.* 41: 3103 (1998). The hydroxyalkanoyl derivatives of privileged structures of this invention include the derivatives of the privileged structures Z1-Z76 listed at page 391 in *J. Comb. Chem.*, 1: 388–396 (1999), excluding lactams (Z29) and benzodiazepine (Z32). Also of interest are the hydroxyalkanoyl derivatives of the following privileged structures:

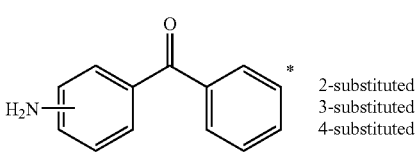

2-substituted
3-substituted
4-substituted

-continued

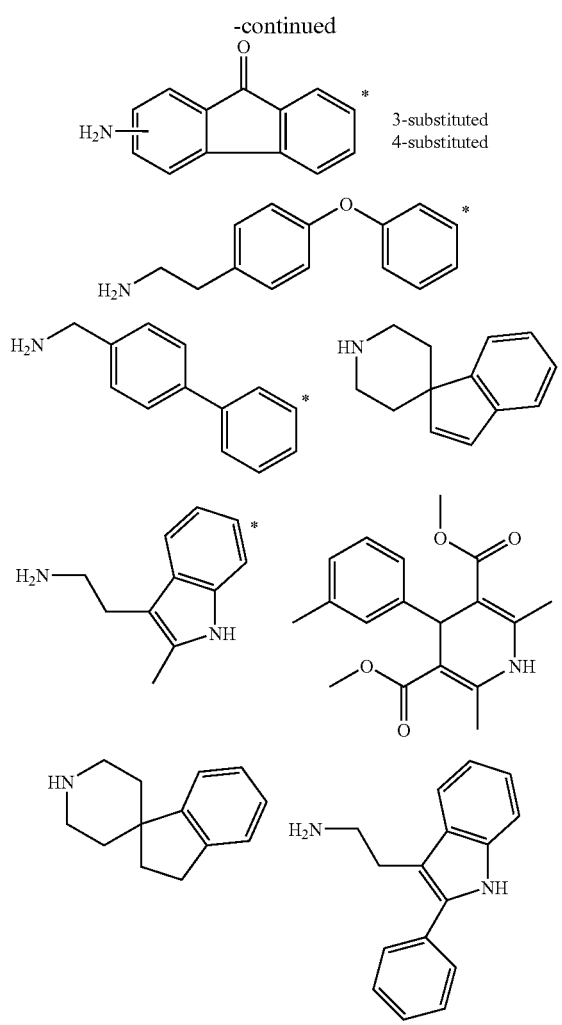

*Amine is commercially available.

Using a variety of privileged structures, the following types of compounds are prepared.

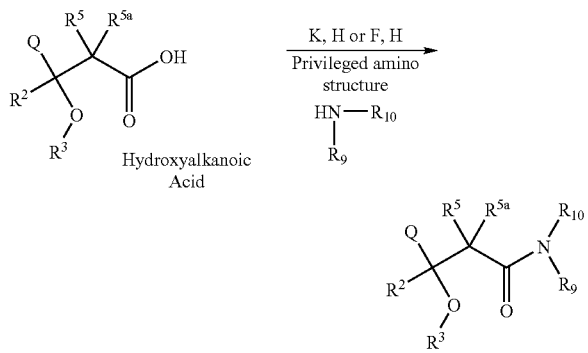

Method K

To a round bottom flask equipped with a magnetic stirbar and N₂ inlet, DMF (30 mL), hydroxyalkanoyl acid (10 mmol), and the amine (10 mmol) are added. The mixture is cooled to 0° C., followed by the addition of triethylamine (TEA), 30 mmol and 1-hydroxybenzotriazole hydrate (HOBT), 26 mmol. The mixture is stirred at 0° C. for 30 min followed by the addition of the 1-ethyl-3-(3'-Dimethylaminopropyl)carbodiimide hydrochloride (EDCI), 13 mmol. The reaction mixture is allowed to warm to room temperature and stirred under N₂ overnight. The reaction mixture is transferred to a separatory funnel and diluted with 30 ml H₂O and extracted with 60 ml ethylacetate. The organic is backwashed by 2×60 ml dilute citric acid, followed by 2×60 ml saturated sodium bicarbonate, followed by 1×60 ml brine and finally dried over MgSO₄, and concentrated in vacuo to yield the desired product.

Construction of Hydroxyalkanoyl Amino Acid Esters:

Using a variety of amino acids esters (natural, unnatural) the following types of compounds can be prepared.

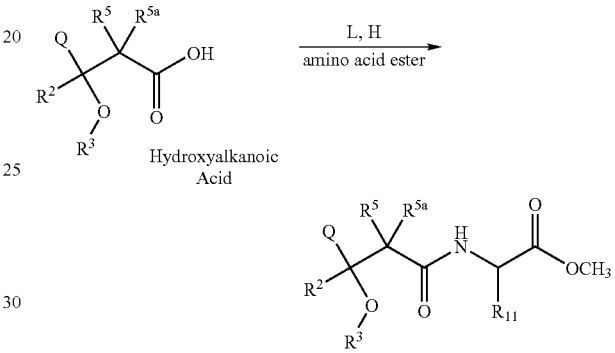

Method L

To a round bottom flask equipped with a magnetic stirbar and N₂ inlet, DMF (30 mL), hydroxyalkanoic acid (10 mmol), and the amino acid ester (10 mmol) are added. The mixture is cooled to 0° C., followed by the addition of triethylamine (TEA), 30 mmol, and 1-hydroxybenzotriazole hydrate (HOBT), 26 mmol. The mixture is stirred at 0° C. for 30 min followed by the addition of the 1-ethyl-3-(3'-Dimethylaminopropyl)carbodiimide hydrochloride (EDCI), 13 mmol. The reaction mixture is allowed to warm to room temperature and stirred under N₂ overnight. The reaction mixture is transferred to a separatory funnel and diluted with 30 ml H₂O and extracted with 60 ml ethylacetate. The combined organic layers are backwashed by 2×60 ml dilute citric acid, followed by 2×60 ml saturated sodium bicarbonate, followed by 1×60 ml brine and finally dried over MgSO₄, and concentrated in vacuo to yield the desired product.

Construction of Hydroxyalkanoyl Anilines

Using a variety of substituted anilines the following types of compounds can be prepared.

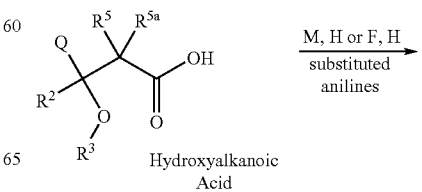

-continued

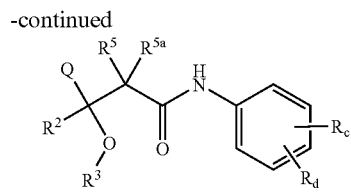

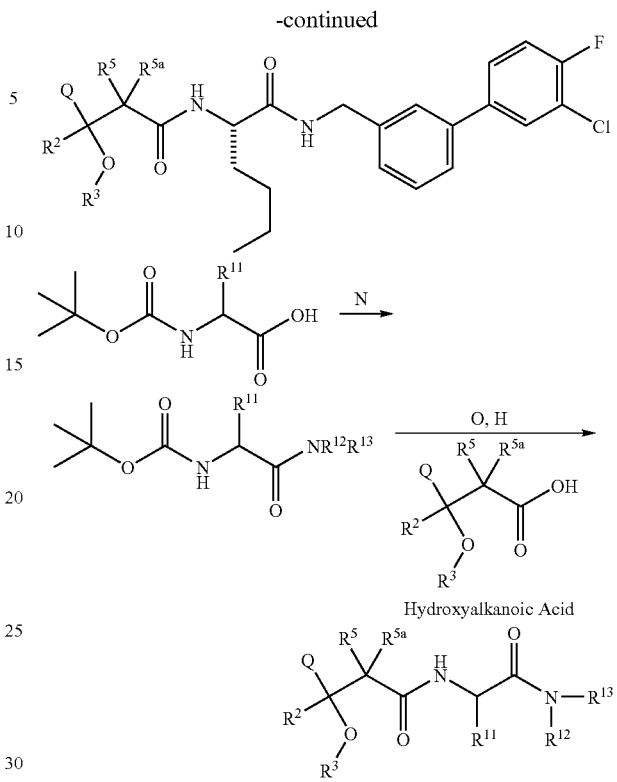

Method M

To a round bottom flask equipped with a magnetic stirbar and $N_2$ inlet was added DMF (30 mL), the hydroxyalkanoic acid (10 mmol), and the aniline (10 mmol) are added. The mixture is cooled to 0° C., followed by the addition of triethylamine (TEA), 30 mmol and 1-hydroxybenzotriazole hydrate (HOBT), 26 mmol. The mixture is stirred at 0° C. for 30 min followed by the addition of the 1-ethyl-3-(3'-Dimethylaminopropyl)carbodiimide hydrochloride (EDCI), 13 mmol. The reaction mixture is allowed to warm to room temperature and stirred under $N_2$ overnight. The reaction mixture is transferred to a separatory funnel and diluted with 30 ml $H_2O$ and extracted with 60 ml ethylacetate. The combined organic layers are backwashed by 2×60 ml dilute citric acid, followed by 2×60 ml saturated sodium bicarbonate, followed by 1×60 ml brine and finally dried over $MgSO_4$, and concentrated in vacuo to yield the desired product.

Construction of Hydroxyalkanoyl Amino Acid Amides:

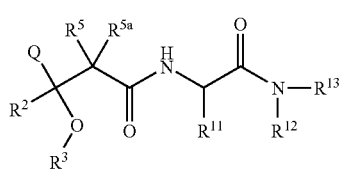

Using a variety of amino acids (natural, unnatural) and a variety of functionalized amines, hydroxyalkanoyl amino acid amides can be prepared. The following three amines ($NR^{12}NR^{13}$) with norleucine as the amino acid (—$NHCHR^{11}CO$—) are preferred compounds.

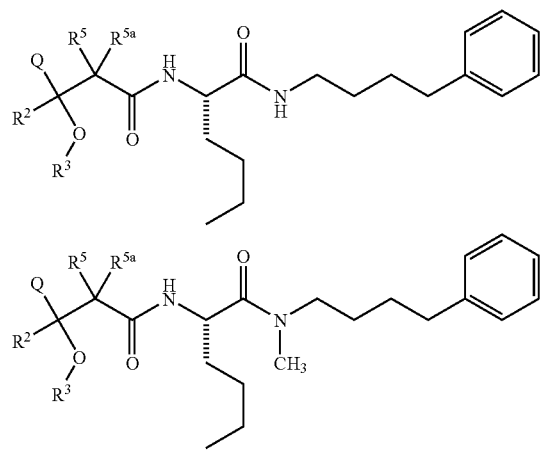

Method N

To a round bottom flask equipped with a magnetic stirbar and $N_2$ inlet was added DMF (30 mL), Boc-Ala-OH, 10 mmol, and the amine, 10 mmol. The mixture was cooled to 0° C., followed by the addition of triethylamine (TEA), 30 mmol and 1-hydroxybenzotriazole hydrate (HOBT), 26 mmol. The mixture was stirred at 0° C. for 30 min followed by the addition of the 1-ethyl-3-(3'-Dimethylaminopropyl) carbodiimide hydrochloride (EDCI), 13 mmol. The reaction mixture was allowed to warm to room temperature and stirred under $N_2$ overnight. The reaction mixture was transferred to a separatory funnel and diluted with 30 ml $H_2O$ and extracted with 60 ml ethylacetate. The combined organic layers were backwashed 2×60 ml dilute citric acid, followed by 2×60 ml saturated sodium bicarbonate, followed by 1×60 ml brine and finally dried over $MgSO_4$, and concentrated in vacuo to yield the desired material.

Method O

Trifluoroacetic acid (TFA), 15 mL was added to carbamate (10 mmol) and stirred at room temperature for 30 minutes. The reaction mixture was concentrated in vacuo to give a yellow oil. To this, DMF (30 ml) and hydroxyalkanoic acid (10 mmol) were added. The mixture was cooled to 0° C., followed by the addition of triethylamine (TEA), 30 mmol, and 1-hydroxybenzotriazole hydrate (HOBT), 26 mmol. The mixture was stirred at 0° C. for 30 min followed by the addition of the 1-ethyl-3-(3'-Dimethylaminopropyl) carbodiimide hydrochloride (EDCI), 13 mmol. The reaction mixture was allowed to warm to room temperature and stirred under $N_2$ overnight. The reaction mixture was transferred to a separatory funnel and diluted with 30 ml $H_2O$ and extracted with 60 ml ethyl acetate. The combined organic layers were backwashed by 2×60 ml dilute citric acid, followed by 2×60 ml saturated sodium bicarbonate, followed by 1×60 ml brine and finally dried over MgSO$_4$, and concentrated in vacuo to yield the desired product.

Construction of Hydroxyalkanoyl Amino Acid Alcohols and Ketones:

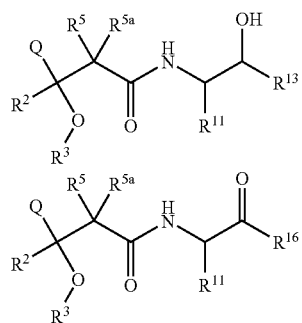

Using a variety of amino acid aldehydes (natural, unnatural) and a variety Grignard reagents (prepared and purchased), hydroxyalkanoyl amino acid alcohols and hydroxyalkanoyl amino acid ketones are prepared. The following amino acid alcohol and ketone structures are preferred.

Method P

Amino acid aldehyde (100M %) was suspended in THF and cooled to 0° C. The Grignard reagent was added dropwise (250M %) and all was allowed to warm to room temperature and stir for 4 hours. The reaction was quenched with dilute aqueous citric acid then extracted with ethyl acetate (3×). The combined organic layers were washed with aqueous NaHCO$_3$ (2×), dried (MgSO$_4$), then solvents evaporated in vacuo. Flash chromatography yielded the desired product.

Method Q

The Dess-Martin reagent, 1,1,1 triacetoxy-1,1-Dihydro-1,2-Benziodoxol-3(1H)-one, 300M %) was added to a solution of CH$_2$Cl$_2$ (50 mL) and the starting alcohol (100M %). This initial mixture was cloudy so enough DMF was added to make the solution homogeneous. All was stirred for 8 hours at which time the reaction was poured into a saturated aqueous solution of NaCl, and extracted with EtOAc (3×). The combined organic layers were washed with aqueous NaHCO$_3$ (2×), brine (1×), dried (MgSO$_4$), then solvents evaporated in vacuo. Flash chromotograpy yielded the desired product.

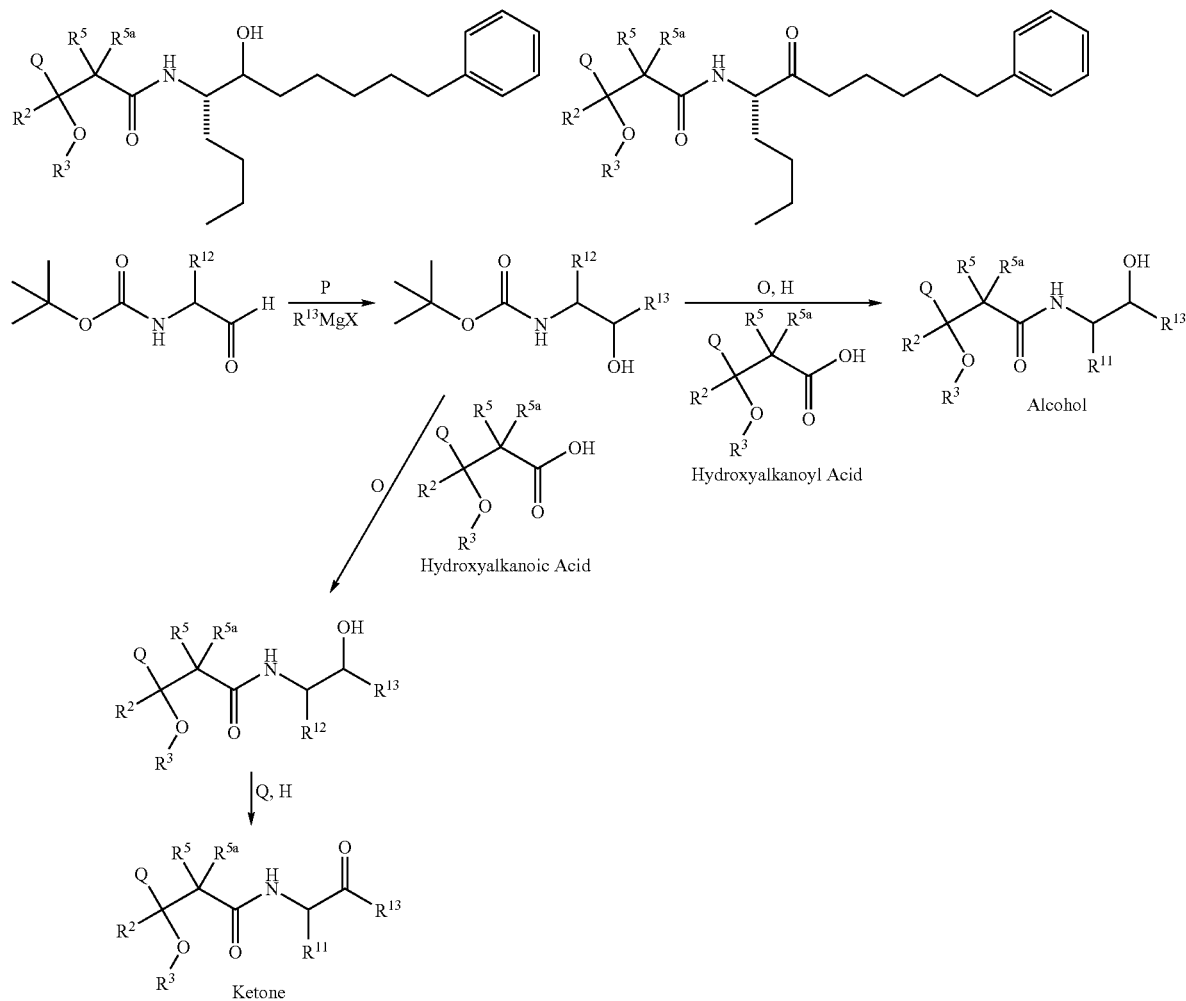

Construction of Hydroxyalkanoyl Amino Hydantoin

Preparation of N-amino-hydantoin

The widely used coupling method in Fmoc protected peptide synthesis is the active ester method, either by in-situ generation, or addition of preformed active ester. The commonly used activated esters are the pentafluorophenyl (OPfp) and 3-hydroxy-2,3-dihydro-4-oxo-benzotriazone (Odhbt). In the presence of HOBt, the rate of reaction is very rapid and efficient with minimal side products. More recently, 1-hydroxy-7-azabenzotriazole (HOAt) and its corresponding uronium salt analog O-(7-azabenzotrizol-1-yl)-1,1,3,3, tetramethyluronium hexafluorophosphate (HATU) have been developed and shown to have a greater catalytic activity than their HOBt and HBTU counterparts, resulting in enhanced coupling yields, shorter coupling times, and greater reduction of racemization. Consequently, these reagents are suitable for coupling sterically hindered amino acids and thereby ensure greater success in the synthesis of difficult peptides and peptidomimetics containing amide bonds. The method utilizing HOAt/HATU for active ester formation is a preferred method of synthesizing N-amino hydantoin.

EXAMPLE 1

N3-Amino-5,5'-diphenyl-imidazolidine-2,4-dione

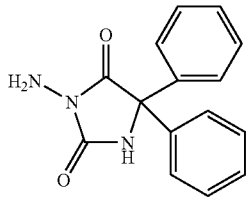

20 g (79.3 mmol) of 5,5'-diphenylydantoin was suspended in 32 mL (0.63 mol) hydrazine monohydrate and refluxed for 7 hours. The reaction mixture was allowed to cool to room temperature. The product crystallized as white precipitate and was separated from the mother liquor via filtration through a glass frit and washed three times with water. The crude material was recrystallized twice from a 9:1 ethanol/water mixture. Yield: 12.6 g (60% of Th.).

LC/MS showed MH$^+$ at 268.2 (exp. 268.2) $t_R$=1.38 min, CH$_3$CN/H$_2$O gradient, [mobile phase A: 0.05% TFA in H20; mobile phase B 0.035% TFQ in CH3CN, column 4.6×50 mm ODC-A: S-5, gradient elution 99:1 A:B to 1:99 A:B, 5.0 min., 3.5 mL/min flow rate].

EXAMPLE 2

N3-Amino-5-benzyl-imidazolidine-2,4-dione

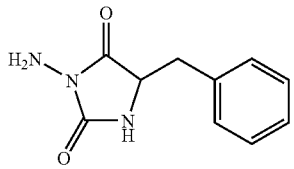

660 mg (4.0 mmol) of L-phenylalanine and 665 mg (5.0 mmol) of tert-butyl-carbazate) were suspended in 7.5 mL quinoline and heated to reflux (~240° C.) for 4 h. The reaction mixture was cooled to room temperature and 10 mL diethylether and 30 mL hexanes were added. The precipitated solid was recrystallized from 2-propanol/water to afford 88 mg (10% of Th.) product.

LC/MS showed MH$^+$ at 205 (exp. 205) $t_R$=1.35 min, CH$_3$CN/H$_2$O gradient, [mobile phase A: 0.05% TFA in H20; mobile phase B 0.035% TFQ in CH3CN, column 4.6×50 mm ODC-A: S-5, gradient elution 99:1 A:B to 1:99 A:B, 5.0 min., 3.5 mL/min flow rate].

EXAMPLE 3

N3-Amino-5-phenyl-imidazolidine-2,4-dione

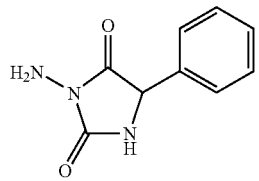

605 mg (4.0 mmol) of L-phenylglycine and 665 mg (5.0 mmol) of tert-butyl-carbazate were suspended in 7.5 mL quinoline (redistilled) and heated to reflux (~240° C.) for 2.5 h. The reaction mixture was cooled to room temperature and diethylether and hexanes were added, resulting in separation of an oil, which solidified on standing overnight. The product was recrystallized from methanol/hexane to afford 171 mg (23% of Th.) product.

LC/MS showed MH$^+$ at 205 (exp. 205) $t_R$=1.35 min, CH$_3$CN/H$_2$O gradient, [mobile phase A: 0.05% TFA in H20; mobile phase B 0.035% TFQ in CH3CN, column 4.6×50 mm ODC-A: S-5, gradient elution 99:1 A:B to 1:99 A:B, 5.0 min., 3.5 mL/min flow rate].

EXAMPLE 4

N3-Amino-N1-phenyl-imidazolidine-2,4-dione

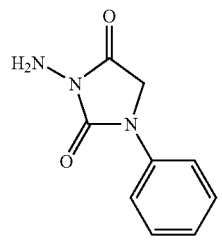

Step 1: Ethyl N-phenylglycinate ethyl carbamate

N-Phenylglycine ethyl ester and 3.0 mL ethylchloroformate were suspended in 100 mL of 2N Na$_2$CO$_3$ and stirred at 50° C. for 15 min. An additional 3.0 mL of ethylchloroformate was added and the reaction stirred for 30 min. Diethylether was added, the organic layer was separated and washed sequentially with 10% aqueous citric acid and 1N NaHCO$_3$ and dried over MgSO$_4$. The solvents were evaporated and the remaining oil was dried under high vacuum to give the intermediate carbamate. Yield: 3.8 g (92% of Th.).

Step 2: 3-Amino-1-phenyl-imidazolidine-2,4-dione

The carbamate prepared above (3.8 g, 15.4 mmol) was dissolved in 6 mL of 1-butanol. Hydrazine monohydrate (1.0 mL, 20 mmol) was added and the reaction mixture was refluxed for 3 h. The product crystallized upon cooling and was recrystallized from ethanol/water as white needles. Yield: 903 mg (29% of Th.)

LC/MS showed MH⁺ at 192.2 (exp. 192) $t_R$=1.75 min, $CH_3CN/H_2O$ gradient, [mobile phase A: 0.05% TFA in H2O; mobile phase B 0.035% TFQ in CH3CN, column 4.6×50 mm ODC-A: S-5, gradient elution 99:1 A:B to 1:99 A:B, 5.0 min., 3.5 mL/min flow rate].

EXAMPLE 5

N3-[(2'S)-Aminopropionamide)-5,5'-diphenyl-imidazolidine-2,4-dione

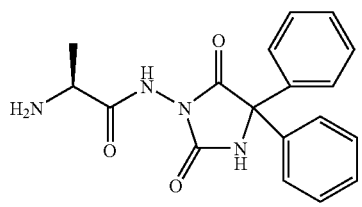

This example shows representative procedures for incorporation of amino-acids (—NH—CH($R_1$)—C(O)—).

2.42 g (9 mmol) of N3-amino-5,5'-diphenyl-imidazoline-2,4-dione and 3.12 g (9.44 mmol) of (L)-Fmoc-Ala-Cl were suspended in 60 mL of dichloromethane. The reaction suspension turned clear within minutes. 1.6 mL (9.44 mmol) of diisopropylethylamine was added and the reaction was stirred under nitrogen for 1 h. Following coupling, the amine was deprotected in situ by addition of 20 mL of diethylamine and stirring for another hour at room temperature. The solvents and the excess base were evaporated, and the residual oil was dissolved in dichloromethane and purified by flash-chromatography using a gradient elution of chloroform/methanol (15:1 to 4:1), affording 2.1 g (6.2 mmol, 68% of Th.) of free amine.

LC/MS showed MH⁺ at 339.2 (exp. 339) $t_R$=2.2 min, $CH_3CN/H_2O$ gradient[mobile phase A: 0.05% TFA in H2O; mobile phase B 0.035% TFQ in CH3CN, column 4.6×50 mm ODC-A: S-5, gradient elution 99:1 A:B to 1:99 A:B, 5.0 min., 3.5 mL/min flow rate].

¹H-NMR (300 MHz, $d_6$-DMSO) □9.25 (s, 1H, NH); 6.9 (m, 10H); 2.35 (s, 1H); 1.9 (m, 2H, $NH_2$); 0.8 (d, 3H).

EXAMPLE 6

N3–[(2'S)-Aminophenylacetamide)-5,5'-diphenyl-imidazolidine-2,4-dione

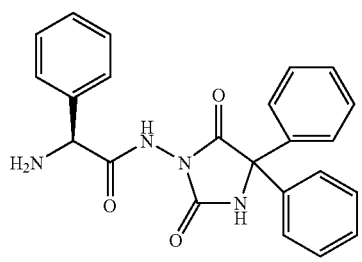

Step 1: 2.5 g (9.35 mmol) of N3-amino-5,5'-diphenyl-imidazoline-2,4-dione and 4.3 g (7.5 mmol) of (L)-Boc-phenylglycine were suspended in 125 mL dichloroethane. HOAt (2.55 g, 18.75 mmol), HATU (7.12 g, 18.74 mmol) and diisopropylethylamine (6.5 mL, 37.3 mmol) were added and the reaction was refluxed under nitrogen for 16 h. The reaction mixture was diluted with EtOAc and washed sequentially with 10% citric acid and brine. Concentration in vacuo gave a thick oil, which was partially purified by flash chromatography using a gradient elution (20–40% EtOAc/hexanes). 2 g of pure product was taken forward.

Step 2: The Boc-protected amine (2.0 g, 4 mmol) was dissolved in 80 mL of dichloromethane and cooled to 0° C. HCl (gas) was bubbled through the solution for 10 minutes. The flask was capped and allowed to warm to rt while stirring overnight. The reaction mixture was sparged with $N_2$ for 20 minutes, then filtered to collect the precipitated amine hydrochloride salt (509 mg, 29%).

LC/MS showed MH⁺ at 401.4 (exp. 401) $t_R$=2.47 min, $CH_3CN/H_2O$ gradient, [mobile phase A: 0.05% TFA in H2O; mobile phase B 0.035% TFQ in CH3CN, column 4.6×50 mm ODC-A: S-5, gradient elution 99:1 A:B to 1:99 A:B, 5.0 min., 3.5 mL/min flow rate]

Pharmaceutical Formulations

When employed as pharmaceuticals, the compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions that contain, as the active ingredient, one or more of the compounds of Formula I, or a pharmaceutically accepted form or prodrug thereof, associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 1 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carriers.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

EXAMPLE 7

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

EXAMPLE 8

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

EXAMPLE 9

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 10

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 11

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

EXAMPLE 12

Suppositories, each containing 25 mg of active ingredient are made as follows:

| Ingredient | Amount |
| --- | --- |
| Active Ingredient | 25 mg |
| Saturated fatty acid glyceride | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 13

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 14

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

EXAMPLE 15

A subcutaneous formulation may be prepared as follows:

| Ingredient | Quantity |
| --- | --- |
| Active Ingredient | 5.0 mg |
| Corn Oil | 1.0 mL |

EXAMPLE 16

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin to | 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mace Publishing Company, Philadelphia, Pa., 17th ed. (1985).

UTILITY

The present invention is directed to a method for inhibiting β-amyloid peptide release and/or synthesis in a cell and a method for inhibiting γ-secretase activity. The invention is also directed to a method for preventing or treating of neurological disorders associated with β-amyloid peptide production. The method comprises the steps of administering to a host in need of such treatment a pharmaceutical formulation comprising a therapeutically effective amount of a compound of Formula I. The compounds of Formula I are useful in the prevention of AD in patients susceptible to AD and/or in the treatment of patients with AD.

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of β-amyloid precursor protein. Compounds that inhibit γ secretase activity, either directly or indirectly, control the production of Aβ. Such inhibition of γ secretase reduces production of Aβ, and is expected to reduce or prevent the neurological disorders associated with Aβ0 such as Alzheimer's Disease.

Compounds of Formula I are expected to possess γ-secretase inhibitory activity or inhibit Aβ production. Cellular screening methods for inhibitors of Aβ production, testing methods for the in vivo suppression of Aβ production, and assays for the detection of secretase activity are known in the art and have been disclosed in many publications, including WO 98/22493 and WO 01/19797, EP 0652009, U.S. Pat. Nos. 5,703,129 5,593,846; 6,211,235 and 6,207,710, all hereby incorporated by reference.

Compounds provided by this invention are useful as standards and reagents in determining the ability of a potential pharmaceutical to inhibit Aβ production. These can be provided in commercial kits comprising a compound of this invention.

A compound is considered to be active if it has an $IC_{50}$ or $K_i$ value of less than about 100 μM for the inhibition of Aβ production.

EXAMPLE 17

β-amyloid Precursor Protein Accumulation Assay

An assay to evaluate the accumulation of Aβ is used to detect potential inhibitors of secretase. The assay uses the N 9 cell line, characterized for expression of exogenous APP by immunoblotting and immunoprecipitation.

The effect of test compounds on the accumulation of Aβ in the conditioned medium is tested by immunoprecipitation as described in WO 01/19797. Briefly, N 9 cells are grown to confluency in the 6-well plates. Test compounds dissolved in DMSO are added together with the addition of radiolabel. The cells are incubated for 4 h at 37° C. in a tissue culture incubator.

At the end of the incubation period, the conditioned medium is harvested and pre-cleared by the addition of normal mouse serum and of protein A Sepharose, mixed by end-over-end rotation for 30 minutes at 4° C., followed by a brief centrifugation in a microfuge. The supernatant is then harvested and transferred to fresh tubes containing of a monoclonal antibody directed against an internal peptide sequence in Aβ and protein A Sepharose. After incubation overnight at 4° C., the samples are washed. The pellet after the last wash is resuspended in SDS sample buffer and boiled for 3 minutes. The supernatant is then fractionated on SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound is considered active if it blocks Aβ accumulation in the conditioned medium, and has and $IC_{50}$ less than 100 μM.

EXAMPLE 18

C-Terminus β-amyloid Precursor Protein Accumulation Assay

The effect of test compounds on the accumulation of C-terminal fragments is determined by immunoprecipitation of APP and fragments thereof from cell lysates as described in WO 01/19797. N 9 cells are metabolically labeled as above in the presence or absence of test compounds. At the end of the incubation period, the conditioned medium are harvested and cells lysed in buffer. Lysates are precleared with normal rabbit serum and protein A-Sepharose, followed by the addition of BC-1 antiserum and protein A-Sepharose for 16 hours at 4° C. The immunoprecipitates are washed bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound is considered active if it stimulates C-terminal fragment accumulation in the cell lysates, and has an $IC_{50}$ less than 100 µM.

EXAMPLE 19

Aβ Immunoprecipitation Assay

This immunoprecipitation assay as described in WO 01/19797 is specific for γ secretase (i.e., proteolytic activity required to generate the C-terminal end of Aβ either by direct cleavage or generating a C-terminal extended species which subsequently further proteolyzed). Briefly, N 9 cells are pulse-labeled in the presence of a reported γ secretase inhibitor for 1 h, followed by washing to remove the radiolabel and the inhibitor. The media is replaced and test compounds are added. Aβ is isolated from the conditioned medium and C-terminal fragments from cell lysates. The test compounds are characterized to determine whether a stabilization of C-terminal fragments is observed and whether Aβ is generated from these accumulated precursor. A typical test compound is considered active if it prevents the generation of Aβ out of accumulated C-terminal fragments and has an $IC_{50}$ less than 100 µM.

EXAMPLE 20

Cellular Screen for the Detection of Inhibitors of β-Amyloid Production

Compounds of Formula I are assayed for their ability to inhibit β-amyloid peptide production in a cell line possessing the Swedish mutation. This screening assay employed cells (K293=human kidney cell line) which were stably transfected with the gene for amyloid precursor protein 751 (APP751) containing the double mutation $Lys_{651}$ $Met_{652}$ to $Asn_{651}$ $Leu_{652}$ (APP751 numbering) in the manner described in WO 94/10569 and Citron et al (*Nature*, 360:672–674 (1992)). This mutation is commonly called the Swedish mutation. The cells, designated as "293 751 SWE", are plated in Corning 96-well plates at $1.5–2.5 \times 10^4$ cells per well in Dulbecco's minimal essential media (Sigma, St. Louis, Mo.) plus 10% fetal bovine serum. Cell number is important in order to achieve β-amyloid ELISA results within the linear range of the assay (about 0.2 to 2.5 ng per mL).

Following overnight incubation at 37° C. in an incubator equilibrated with 10% carbon dioxide, media were removed and replaced with 200 µL of a compound of formula I (drug) containing media per well for a two hour pretreatment period and cells were incubated as above. Drug stocks were prepared in 100% dimethyl sulfoxide such that at the final drug concentration used in the treatment, the concentration of dimethyl sulfoxide did not exceed 0.5% and, in fact, usually equaled 0.1%.

At the end of the pretreatment period, the media are again removed and replaced with fresh drug containing media as above and cells are incubated for an additional two hours. After treatment, plates are centrifuged in a Beckman GPR at 1200 rpm for five minutes at room temperature to pellet cellular debris from the conditioned media. From each well, 100 µL of conditioned media or appropriate dilutions thereof are transferred into an ELISA plate precoated with antibody 266 (*Nature*, 359:325–327 (1992)) against amino acids 13–28 of β-amyloid peptide as described in WO 94/10569 and stored at 4° C. overnight. An ELISA assay employing labelled antibody 6C6 (*Nature*, 359:325–327 (1992)) against amino acids 1–16 of β-amyloid peptide is run the next day to measure the amount of β-amyloid peptide produced.

Cytotoxic effects of the compounds are measured by a modification of the method of Hansen, et al. (*J. Immun. Meth.*, 119:203–210 (1989)). To the cells remaining in the tissue culture plate is added 25 µL of a 3-(4,5-dimethylthiazol-2-yl)-2,5-diphenyltetrazolium bromide (MTT) (Sigma, St. Louis, Mo.) stock solution (5 mg/mL) to a final concentration of 1 mg/mL. Cells are incubated at 37° C. for one hour, and cellular activity was stopped by the addition of an equal volume of MTT lysis buffer (20% w/v sodium dodecylsulfate in 50% dimethylformamide, pH 4.7). Complete extraction is achieved by overnight shaking at room temperature. The difference in the $OD_{562}$ nm and the $OD_{650}$ mn is measured in a Molecular Device's $UV_{max}$ microplate reader as an indicator of the cellular viability.

The results of the β-amyloid peptide ELISA are fit to a standard curve and expressed as ng/mL β-amyloid peptide. In order to normalize for cytotoxicity, these results are divided by the MTT results and expressed as a percentage of the results from a drug free control.

EXAMPLE 21

In Vivo Suppression of β-Amyloid Release and/or Synthesis

This example illustrates how the compounds of this invention could be tested for in vivo suppression of β-amyloid release and/or synthesis. For these experiments, 3 to 4 month old PDAPP mice are used (Games et al., Nature 373:523–52 (1995)). Depending upon which compound is being tested, the compound is usually formulated at either 5 or 10 mg/ml. Because of the low solubility factors of the compounds, they may be formulated with various vehicles, such as corn oil (Safeway, South San Francisco, Calif.); 10% EtOH in corn oil (Safeway); 2-hydroxypropyl-β-cyclodextrin (Research Biochemicals International, Natick Mass.); and carboxy-methyl-cellulose (Sigma Chemical Co., St. Louis, Mo.).

The mice are dosed subcutaneously with a 26 gauge needle and 3 hours later the animals are euthanized via $CO_2$ narcosis and blood is taken by cardiac puncture using a 1 cc 25G ⅝" tuberculin syringe/needle coated with solution of 0.5 M EDTA, pH 8.0. The blood is placed in a Becton-Dickinson vacutainer tube containing EDTA and spun down for 15 minutes at 1500×g at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid.

The brain homogenates are diluted 1:10 with ice-cold casein buffer (0.25% casein, phosphate buffered saline (PBS), 0.05% sodium azide, 20 µg/ml aprotinin, 5 mM EDTA, pH 8.0, 10 .mu.g/ml leupeptin), thereby reducing the final concentration of guanidine to 0.5 M, before centrifugation at 16,000×g for 20 minutes at 4° C. The β-amyloid standards (1–40 or 1–42 amino acids) were prepared such that the final composition equaled 0.5 M guanidine in the presence of 0.1% bovine serum albumin (BSA).

The total β-amyloid sandwich ELISA, quantitating both β-amyloid (aa 1–40) and β-amyloid (aa 1–42) consists of two monoclonal antibodies (mAb) to β-amyloid. The capture antibody, 266, is specific to amino acids 13–28 of β-amyloid. The antibody 3D6, which is specific to amino acids 1–5 of β-amyloid, is biotinylated and served as the reporter antibody in the assay. The 3D6 biotinylation procedure employs the manufacturer's (Pierce, Rockford Ill.) protocol for NHS-biotin labeling of immunoglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of about 50 pg/ml (11 pM) and shows no cross-reactivity to the endogenous murine .beta.-amyloid peptide at concentrations up to 1 ng/ml.

The configuration of the sandwich ELISA quantitating the level of β-amyloid (aa 1–42) employs the mAb 21F12 (which recognizes amino acids 33–42 of β-amyloid) as the capture antibody. Biotinylated 3D6 is also the reporter antibody in this assay which has a lower limit of sensitivity of about 125 pg/ml (28 pM).

The 266 and 21F12 capture mAbs are coated at 10 µg/ml into 96 well immunoassay plates (Costar, Cambidge Mass.) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed three times with wash buffer between each step of the assay. The biotinylated 3D6, diluted to 0.5 µg/ml in casein incubation buffer (0.25% casein, PBS, 0.05% Tween 20, pH 7.4) is incubated in the well for 1 hour at room temperature. Avidin-HRP (Vector, Burlingame Calif.) diluted 1:4000 in casein incubation buffer is added to the wells for 1 hour at room temperature. The colorimetric substrate, Slow TMB-ELISA (Pierce, Cambridge, Mass.), is added and allowed to react for 15 minutes, after which the enzymatic reaction is stopped with addition of 2 N $H_2SO_4$. Reaction product is quantified using a Molecular Devices Vmax (Molecular Devices, Santa Clara, Calif.) measuring the difference in absorbance at 450 nm and 650 nm.

2. Blood Assay

The EDTA plasma is diluted 1:1 in specimen diluent (0.2 gm/l sodium phosphate.$H_2O$ (monobasic), 2.16 gm/l sodium phosphate.$7H_2O$ (dibasic), 0.5 gm/l thimerosal, 8.5 gm/l sodium chloride, 0.5 ml Triton X-405, 6.0 g/l globulin-free bovine serum albumin; and water). The samples and standards in specimen diluent are assayed using the total β-amyloid assay (266 capture/3D6 reporter) described above for the brain assay except the specimen diluent is used instead of the casein diluents described.

Although the invention has been described with reference to the presently preferred embodiments, it should be understood that various modifications can be made without departing from the spirit of the invention.

What is claimed is:

1. A compound of Formula I:

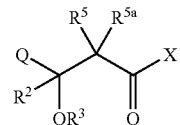

Formula I or a pharmaceutically acceptable salt form or thereof, wherein X is

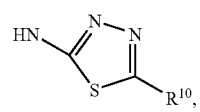

Q is $Q^1$,
(C$_1$–C$_3$ alkyl)-O-$Q^1$,
(C$_1$–C$_3$ alkyl)-S-$Q^1$,
(C$_1$–C$_3$ alkyl)-S(=O)-$Q^1$,
(C$_1$–C$_3$ alkyl)-S(=O)$_2$-$Q^1$, or ($C_1$–$C_3$ alkyd)-N ($R^{20}$)-$Q^1$;
$Q^1$ is $C_1$–$C_6$ alkyl;
($C_2$–$C_6$ alkenyl substituted with 0–3 $R^{1a}$;
($C_2$–$C_6$ alkynyl substituted with 0–3 $R^{1a}$;
$C_3$–$C_{10}$ cycloalkyl substituted with 0–3 $R^{1b}$;
$C_3$–$C_{10}$ carbocycle substituted with 0–3 $R^{1b}$; or
$C_6$–$C_{10}$ aryl substituted with 0–3 $R^{1b}$;
$R^{10}$ is $C_1$–$C_6$ alkyl substituted with 0–3 $R^{1a}$;
($C_2$–$C_6$ alkenyl substituted with 0–3 $R^{1a}$;
($C_2$–$C_6$ alkynyl substituted with 0–3 $R^{1a}$;
$C_3$–$C_{10}$ cycloalkyl substituted with 0–3 $R^{1b}$;
$C_3$–$C_{10}$ carbocycle substituted with 0–3 $R^{1b}$; or
$C_6$–$C_{10}$ aryl substituted with 0–3 $R^{1b}$;
$R^{1a}$, at each occurrence, is independently selected from the group consisting of:
H, $C_1$–$C_6$ alkyl, $OR^{14}$, Cl, F, Br, I, $NR^{15}R^{16}$, $CF_3$;
$C_3$–$C_{10}$ carbocycle substituted with 0–3 $R^{1b}$; and
$C_6$–$C_{10}$ aryl substituted with 0–3 $R^{1b}$;
$R^{1b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, and ($C_1$–$C_6$ alkyl)-O—C (=O)—;
$R^2$ is H, methyl, ethyl, propyl, or butyl;
$R^3$ is H, $C_1$–$C_4$ alkyl, —C(=O)($C_1$–$C_4$ alkyl), or —C(=S)($C_1$–$C_4$ alkyl);
$R^5$ is H, $OR^{14}$;
$C_1$–$C_6$ alkyl substituted with 0–3 $R^{5b}$;
$C_1$–$C_6$ alkoxy substituted with 0–3 $R^{5b}$;
($C_2$–$C_6$ alkenyl substituted with 0–3 $R^{5b}$;
($C_2$–$C_6$ alkynyl substituted with 0–3 $R^{5b}$;
$C_3$–$C_{10}$ cycloalkyl substituted with 0–3 $R^{5c}$;
$C_3$–$C_{10}$ carbocycle substituted with 0–3 $R^{5c}$; or
$C_6$–$C_{10}$ aryl substituted with 0–3 $R^{5c}$;
$R^{5a}$ is H, $C_1$–$C_4$ alkyl, or $C_2$–$C_4$ alkenyl;
$R^{5b}$ at each occurrence, is independently selected from the group consisting of:
H, $C_1$–$C_6$ alkyl, $CF_3$, $OR^{14}$, Cl, F, Br, I, =O, CN, $NO_2$, $NR^{15}R^{16}$, acetyl, $SCH_3$, S(=O)$CH_3$, S(=O)$_2CH_3$, ($C_2$–$C_6$ alkenyl, ($C_2$–$C_6$ alkynyl, $C_1$–$C_4$ alkoxy, $C_1$–$C_4$ haloalkyl, $C_1$–$C_4$ haloalkoxy, and $C_1$–$C_4$ haloalkyl-S—,
$C_3$–$C_{10}$ cycloalkyl substituted with 0–3 $R^{5c}$;
$C_3$–$C_{10}$ carbocycle substituted with 0–3 $R^{5c}$; and
$C_6$–$C_{10}$ aryl substituted with 0–3 $R^{5c}$;
$R^{5c}$, at each occurrence, is independently selected from the group consisting of H, OH, Cl, F, Br, I, CN, $NO_2$, $NR^{15}R^{16}$, $CF_3$, acetyl, $SCH_3$, S(=O)$CH_3$, S(=O)$CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
$R^{14}$, at each occurrence, is independently selected from the group consisting of H, phenyl, benzyl, $C_1$–$C_6$ alkyl, and ($C_2$–$C_6$ alkoxyalkyl);
$R^{15}$, at each occurrence, is independently selected from the group consisting of H, $C_1$–$C_6$ alkyl, phenyl, benzyl, phenethyl, ($C_1$–$C_6$ alkyl)-C(=O)—, ($C_1$–$C_6$ alkyl)—O—C(=O)— and ($C_1$–$C_6$ alkyl)-S(=O)$_2$—; and
$R^{16}$, at each occurrence, is independently selected from the group consisting of H, $C_1$–$C_6$ alkyl, phenyl, benzyl, phenethyl, ($C_1$–$C_6$ alkyl)—C(=O)—, ($C_1$–$C_6$ alkyl)—O—C(=O)— and ($C_1$–$C_6$ alkyl)-S(=O)$_2$—.

2. The compound according to claim 1, wherein $R^{10}$ is —C($CH_3$)$_2$ phenyl.

3. The compound according to claim 1 or 2, wherein Q is —$CH_3$, —$CH_2CH_3$, —$CH_2CH_2CH_3$, —$CH_2CH_2CH_2CH_3$, —$CH_2CH_2CH_2CH_3$, —$CH_2CH_2CH_2CH_2CH_3$, —$CH_2CH_2CH_2CH_2CH_2CH_3$, —CH($CH_3$)$_2$, —CH($CH_3$)$CH_2CH_3$, —$CH_2CH(CH_3)_2$, —$CH_2C(CH_3)_3$, —CH=$CH_2$, —$CH_2CH$=$CH_2$, —$CH_2C(CH_3)$=$CH_2$, —$CH_2CH_2CH$=$CH_2$, —$CH_2CH_2C(CH_3)$=$CH_2$, cis-$CH_2CH$=CH($CH_3$), cis-$CH_2CH_2CH$=CH($CH_3$); trans-$CH_2CH$=CH($CH_3$), trans $CH_2CH_2CH$=CH($CH_3$), —C≡CH, —$CH_2C$≡CH, —$CH_2C$≡C($CH_3$),
cyclopropyl-, cyclobutyl-, cyclopentyl-, cyclohexyl-, phenyl-, 2-F-phenyl-, 3-F-phenyl-, 4-F-phenyl-, 4-methoxyphenyl-, 4-ethoxyphenyl-, 4 propoxyphenyl-,
$R^2$ is H or methyl;
$R^5$ is —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2CH(CH_3)_2$, —$CH_2C(CH_3)_3$, —$CH_2CH_2CH_2CH_2CH_3$, —CH($CH_3$)$CH_2H_2CH_3$, —$CH_2CH(CH_3)CH_2CH_3$, —$CH_2CH_2CH(CH_3)_2$, —CH($CH_2CH_3$)$_2$, —$CF_3$, —$CH_2CF_3$, —$CH_2CH_2CF_3$, —$CH_2CH_2CH_2CH_3$, —$CH_2CH_2CH_2CH_2CF_3$, —CH=$CH_2$, —$CH_2CH$=$CH_2$, —$CH_2CH_2CH$=CH=$CH_2$, —CH=$CHCH_3$, cis-$CH_2CH$=CH ($CH_3$), trans-$CH_2CH$=CH($CH_3$), trans-$CH_2CH$=CH($C_6H_5$), —$CH_2CH$=C($CH_3$)$_2$, cis-$CH_2CH$=$CHCH_2CH_3$, trans-$CH_2CH$=$CHCH_2CH_3$, cis-$CH_2CH_2CH$=CH ($CH_3$), trans-$CH_2CH_2CH$=CH($CH_3$), trans-$CH_2CH$=$CHCH_2$($C_6H_5$),
—C≡CH, —$CH_2C$≡CH, —$CH_2C$≡C($CH_3$), —$CH_2C$≡C($C_6H_5$), —$CH_2CH_2C$≡CH, —$CH_2CH_2C$≡C($CH_3$), —$CH_2CH_2C$≡C($C_6H_5$), —$CH_2CH_2CH_2C$≡CH, —$CH_2CH_2CH_2C$≡C ($CH_3$), —$CH_2CH_2CH_2C$≡C($C_6H_5$),
cyclopropyl-$CH_2$—, cyclobutyl-$CH_2$—, cyclopentyl-$CH_2$—, cyclohexyl-$CH_2$—, (2-$CH_3$-cyclopropyl)$CH_2$—, (3-$CH_3$-cyclobutyl)$CH_2$—, cyclopropyl-$CH_2CH_2$—, cyclobutyl-$CH_2CH_2$—, cyclopentyl-$CH_2CH_2$—, cyclohexyl-$CH_2CH_2$—, (2-$CH_3$-cyclopropyl)$CH_2CH_2$—, (3-$CH_3$-cyclobutyl)$CH_2CH_2$—,
phenyl-$CH_2$—, (2-F-phenyl)$CH_2$—, (3-F-phenyl)$CH_2$—, (4-F-phenyl)$CH_2$—, (3,5-diF-phenyl)$CH_2$—,
phenyl-$CH_2CH_2$—, (2-F-Phenyl)$CH_2CH_2$—, (3-F-phenyl)$CH_2CH_2$—, (4-F-phenyl)$CH_2CH_2$—,
methoxy, ethoxy, propoxy, or butoxy; and
$R^{5a}$ is H.

4. The compound according to claim 1, wherein $R^5$ is $C_3$–$C_{10}$ carbocycle substituted with 0–3 $R^{5c}$.

5. The compound according to claim 1, wherein Q is —$CH_3$, —$CH_2CH_3$, —$CH_2CH_2CH_3$, —$CH_2CH_2CH_2CH_3$, —$CH_2CH_2CH_2CH_3$, —$CH_2CH_2CH_2CH_2CH_3$, —$CH_2CH_2CH_2CH_2CH_2CH_3$, —CH($CH_3$)$_2$, —CH($CH_3$)$CH_2CH_3$, —$CH_2CH(CH_3)_2$, —$CH_2C(CH_3)$.

6. The compound according to claim 1, wherein $R^{10}$ is $C_1$–$C_6$ alkyl substituted with 0–3 $R^{1a}$.

7. The compound according to claim 1, wherein
$R^{10}$ is —C($CH_3$)$_2$ phenyl;
$R^5$ is $C_3$–$C_{10}$ carbocycle;
$R^{5a}$ is H;
Q=$Q^1$=methyl;
$R^2$=H; and
$OR^3$=OH.

* * * * *

SEQUENCE LISTING

```
<160> NUMBER OF SEQ ID NOS: 1

<210> SEQ ID NO 1
<211> LENGTH: 43
<212> TYPE: PRT
<213> ORGANISM: human

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40
```